US011840736B2

(12) United States Patent
Schneider et al.

(10) Patent No.: US 11,840,736 B2
(45) Date of Patent: Dec. 12, 2023

(54) NUCLEIC ACID BIOMARKER AND USE THEREOF

(71) Applicants: Daiichi Sankyo Co., Ltd., Tokyo (JP); U3 Pharma GmbH, Martinsried (DE); AMGEN, INC., Thousand Oaks, CA (US)

(72) Inventors: Matthias Schneider, Neufarn (DE); Sabine Blum, Munich (DE); Renee Jeanne Mendell-Harary, Skillman, NJ (US); Daniel J. Freeman, Holmdel, NJ (US); Robert Allen Beckman, Blue Bell, PA (US); Xiaoping Jin, Hillsborough, NJ (US)

(73) Assignees: Daiichi Sankyo Co., Ltd., Tokyo (JP); U3 Pharma GmbH, Martinsried (DE); Amgen, Inc., Thousand Oaks, CA (US)

( * ) Notice: Subject to any disclaimer, the term of this patent is extended or adjusted under 35 U.S.C. 154(b) by 468 days.

(21) Appl. No.: 16/547,434

(22) Filed: Aug. 21, 2019

(65) Prior Publication Data

US 2020/0140954 A1 May 7, 2020

Related U.S. Application Data

(63) Continuation of application No. 15/297,775, filed on Oct. 19, 2016, now abandoned, which is a continuation of application No. 14/502,792, filed on Sep. 30, 2014, now abandoned.

(60) Provisional application No. 61/884,982, filed on Sep. 30, 2013.

(51) Int. Cl.
| | |
|---|---|
| *G01N 33/574* | (2006.01) |
| *A61K 39/395* | (2006.01) |
| *C12Q 1/6886* | (2018.01) |
| *C07K 16/32* | (2006.01) |
| *C07K 16/28* | (2006.01) |
| *A61K 45/06* | (2006.01) |
| *A61K 39/00* | (2006.01) |

(52) U.S. Cl.
CPC ...... *C12Q 1/6886* (2013.01); *A61K 39/39558* (2013.01); *A61K 45/06* (2013.01); *C07K 16/2863* (2013.01); *C07K 16/32* (2013.01); *A61K 2039/505* (2013.01); *C07K 2317/73* (2013.01); *C12Q 2600/106* (2013.01); *C12Q 2600/158* (2013.01); *G01N 2333/4704* (2013.01)

(58) Field of Classification Search
CPC .......... A61K 39/39558; C07K 16/2863; A61P 35/00
See application file for complete search history.

(56) References Cited

U.S. PATENT DOCUMENTS

| | | | |
|---|---|---|---|
| 2008/0172184 A1 | 7/2008 | Chaires et al. | |
| 2011/0027291 A1* | 2/2011 | Schoeberl | A61P 35/00 703/2 |
| 2011/0229493 A1 | 9/2011 | Jackson et al. | |
| 2011/0236903 A1* | 9/2011 | McClelland | C12Q 1/6886 435/6.1 |
| 2012/0015827 A1 | 1/2012 | Wirtz | |

FOREIGN PATENT DOCUMENTS

| | | |
|---|---|---|
| WO | WO 2013/023043 A2 | 2/2013 |
| WO | WO2013/052745 A1 | 4/2013 |

OTHER PUBLICATIONS

MacCallum et al J. Mol. Biol., 262, 732-745, 1996.*
Li et al Discov Med, 16:79-92, Sep. 2013.*
Biomarkers Definitions Working Group, "Biomarkers and surrogate endpoints: Preferred definitions and conceptual framework," Clinical Pharmacology and Therapeutics, vol. 69, No. 3, Mar. 2001, pp. 89-95.
Cho, "Contribution of oncoproteomics to cancer biomarker discovery," Molecular Cancer, vol. 6, No. 25, 2007, 13 pages.
Engelman, et al. "The role of the ErbB family members in non-small cell lung cancers sensitive to epidermal growth factor receptor kinase inhibitors." Clinical Cancer Research, vol. 12, Jul. 2006, pp. 4372s-4376s.
Garner et al., "An antibody that locks HER3 in the inactive conformation inhibits tumor growth driven by HER2 or neuregulin," Cancer Research, vol. 73, No. 19, Aug. 2013, pp. 6024-6035.
International Search Report issued in corresponding application No. PCT/US2014/058437 dated Apr. 13, 2015.
Ritter, et al. "Human Breast Cancer Cells Selected for Resistance to Trastuzumab In vivo Overexpress Epidermal Growth Factor Receptor and ErbB Ligands and Remain Dependent on the ErbB Receptor Network" Clinical Cancer Research, vol. 13, No. 16, Aug. 2007, pp. 4909-4919.
Sawyers, "The cancer biomarker problem," Nature, vol. 452, Apr. 2008, pp. 548-552.
Sergina, et al. "Escape from HER-family tyrosine kinase inhibitor therapy by the kinase-inactive HER3" vol. 445, Nature, 2007, pp. 437-441.

(Continued)

*Primary Examiner* — Mark Halvorson
(74) *Attorney, Agent, or Firm* — Foley & Lardner LLP

(57) ABSTRACT

The present invention is directed to methods of identifying and treating a human subject harboring a tumor or other disease comprising assessing HRG gene expression at an mRNA level in the human subject and administering a treatment comprising an anti-HER3 antibody to the human subject whose HRG gene expression at an mRNA level is assessed as high. The present invention is also directed to methods of identifying a human subject harboring a tumor or other disease comprising assessing HRG gene expression at an mRNA level in the human subject and withholding a treatment comprising an anti-HER3 antibody to the human subject whose HRG gene expression at an mRNA level is assessed as low.

14 Claims, 15 Drawing Sheets

(56) References Cited

OTHER PUBLICATIONS

Paul, Fundamental Immunology, 3$^{rd}$ Edition, 1993, pp. 292-295.
Rudikoff et al., Proc. Natl. Acad. Sci., vol. 79, No. 6, pp. 1979-1983 (1982).
Coleman, Research Immunology, vol. 145, pp. 33-36 (1994).

\* cited by examiner

NUCLEIC ACID BIOMARKER AND USE THEREOF

FIELD OF THE INVENTION

The field of the invention is molecular biology, oncology, clinical diagnostics, and clinical treatment.

BACKGROUND

Most cancer drugs are effective in some patients, but not in others. This results from genetic variation among tumors, and can be observed even among tumors within the same patient. Variable patient response is particularly pronounced with respect to targeted therapeutics. Therefore, the full potential of targeted therapies cannot be realized without suitable tests for determining which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention." (Biomarkers Definitions Working Group, 2001, Clin. Pharmacol. Ther. 69:89-95)

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states: "There is a critical need for expedited development of biomarkers and their use to improve diagnosis and treatment of cancer." (Cho, 2007, Molecular Cancer 6:25) Another recent review article on cancer biomarkers contains the following comments: "The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, Nature 452:548-552, at 548) Comments such as the foregoing illustrate the recognition of a need for the discovery of clinically useful biomarkers and diagnostic methods based on such biomarkers.

There are three distinct types of cancer biomarkers: (1) prognostic biomarkers, (2) predictive biomarkers, and (3) pharmacodynamic biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2) gene is amplified are likely to benefit from treatment with trastuzumab (HERCEPTIN®), whereas patients without ERBB2 gene amplification are unlikely to benefit from treatment with trastuzumab. A pharmacodynamic biomarker is an indication of the effect(s) of a drug on its molecular target while the patient is taking the drug. Accordingly, pharmacodynamic biomarkers often are used to guide dosage level and dosing frequency, during the early stages of clinical development of a new drug. For a discussion of cancer biomarkers, see, e.g., Sawyers, 2008, Nature 452:548-552.

Tumors driven by EGFR or HER2 often respond to treatment with inhibitors of EGFR or HER2, but these tumors invariably develop resistance to these inhibitors. At least one mechanism of acquired resistance to anti-EGFR or anti-HER2 treatment is activation of HER3 (also known as ERBB3) signaling. See, e.g., Engelman et al, 2006, Clin. Cancer Res. 12:4372; Ritter et al, 2007, Clin. Cancer Res. 13:4909; Sergina et al, 2007, Nature 445:437. HER3 plays an important role in development of drug resistance, as well as being involved in tumor initiation and maintenance, through its heterodimerization with EGFR and HER2. Consequently, there has been interest in development of HER3 inhibitors, especially anti-HER3 antibodies, since HER3 lacks kinase activity.

As with other types of targeted therapy, some, but not all, tumors respond to anti-HER3 therapy. Therefore, there is a need for diagnostic methods based on predictive biomarkers that can be used to identify patients with tumors that are likely (or unlikely) to respond to treatment with a HER3 inhibitor such as an anti-HER3 antibody.

SUMMARY

The present invention is directed to methods of treating a human subject harboring a locally advanced or metastatic non-small cell lung cancer (NSCLC) tumor comprising administering a treatment comprising an anti-HER3 antibody to a human subject diagnosed with a locally advanced or metastatic NSCLC whose HRG gene expression at an mRNA level is assessed as high.

Some embodiments comprise assessing HRG gene expression at an mRNA level in a human subject diagnosed with a locally advanced or metastatic NSCLC and administering a treatment comprising an anti-HER3 antibody to a human subject whose HRG gene expression at an mRNA level is assessed as high.

Some embodiments comprise ordering an assessment of HRG gene expression at an mRNA level in a human subject diagnosed with a locally advanced or metastatic NSCLC and administering a treatment comprising an anti-HER3 antibody to the human subject whose HRG gene expression at an mRNA level is assessed as high.

In a particular embodiment of the invention, the HRG gene expression at an mRNA level is assessed as high if a delta Ct (dCt) value is observed, which is below a predetermined threshold, from a biological sample taken from the subject diagnosed with a locally advanced or metastatic NSCLC.

In some embodiments, the predetermined threshold is chosen statistically to minimize undesirable effects of false positives and false negatives. In some embodiments, the predetermined threshold dCt value is in a range of from about 2.7 to about 4.1. In a preferred embodiment, the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

In some embodiments, the subject harbors wild-type EGFR. In preferred embodiments, the subject has also progressed on at least one prior systemic therapy. In more preferred embodiments, a tumor tissue or fragment thereof for or with which the HRG gene expression is assessed has been removed from the subject prior to any (systemic) therapy.

Some embodiments comprise assessing HRG gene expression at an mRNA level in a human subject diagnosed with a locally advanced or metastatic NSCLC, where HRG gene expression at an mRNA level is assessed using quantitative reverse transcriptase polymerase chain reaction (qRT-PCR).

In some embodiments, the biological sample comprises a tumor sample.

In some embodiments, the anti-HER3 antibody is selected from the group consisting of patritumab, duligotumab (MEHD-7945A), seribantumab (MM-121), MM-111, LJM716, RG-7116, tri-specific anti-EGFR/ERBB3 zybody, huHER3-8, or a derivative or fragment of any of these.

In some embodiments, the treatment comprises an anti-HER3 antibody in combination with one or more of (i) a HER inhibitor, (ii) a chemotherapy, (iii) radiation, and (iv) an other targeted agent.

For example, In some embodiments the HER inhibitor is selected from the group consisting of trastuzumab, T-DM1, lapatinib, pertuzumab, cetuximab, panitumumab gefitinib, afatinib, dacomitinib, KD-019 and erlotinib.

In some embodiments, the chemotherapy is selected from the group consisting of cisplatin, carboplatin, gemcitabine, pemetrexed, irinotecan, 5-fluoruracil, paclitaxel, docetaxel, and capecitabine. However, other chemotherapies can be applied.

The present invention is also directed to methods of treating a human subject harboring a locally advanced or metastatic non-small cell lung cancer (NSCLC) tumor comprising assessing HRG gene expression at an mRNA level in a human subject diagnosed with a locally advanced or metastatic NSCLC, and withholding a treatment comprising an anti-HER3 antibody to a human subject whose HRG gene expression at an mRNA level is assessed as low.

Some embodiments comprise ordering an assessment of an HRG gene expression at an mRNA level in a human subject diagnosed with a locally advanced or metastatic NSCLC and withholding a treatment comprising an anti-HER3 antibody to the human subject whose HRG gene expression at an mRNA level is assessed as low.

In some embodiments, the HRG gene expression at an mRNA level is assessed as low if a delta Ct (dCt) value is observed, which is at or above a predetermined threshold, from a biological sample taken from the subject diagnosed with a locally advanced or metastatic NSCLC.

In some embodiments, the predetermined threshold is chosen statistically to minimize undesirable effects of false positives and false negatives. In some embodiments, the predetermined threshold dCt value is in a range of from about 2.7 to about 4.1. In some embodiments, the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

In some embodiments, the subject harbors wild-type EGFR. In preferred embodiments, the tumor has progressed on at least one prior systemic therapy. In more preferred embodiments, a tumor tissue or fragment thereof for or with which the HRG gene expression is assessed has been removed from the subject prior to any (systemic) therapy.

In some embodiments, HRG gene expression at an mRNA level is assessed using quantitative reverse transcriptase polymerase chain reaction (qRT-PCR).

In some embodiments, the biological sample comprises a tumor sample.

In some embodiments, the treatment withheld comprises an anti-HER3 antibody in combination with one or more of (i) a HER inhibitor, (ii) a chemotherapy, (iii) radiation, and (iv) an other targeted agent.

Some embodiments comprise treating a human subject whose HRG gene expression at an mRNA level is assessed as low with a HER inhibitor selected from the group consisting of trastuzumab, T-DM1, lapatinib, pertuzumab, cetuximab, panitumumab gefitinib, afatinib, dacomitinib, KD-019 and erlotinib.

Some embodiments comprise treating a human subject whose HRG gene expression at an mRNA level is assessed as low with a chemotherapy selected from the group consisting of cisplatin, carboplatin, gemcitabine, pemetrexed, irinotecan, 5-fluoruracil, paclitaxel, docetaxel, and capecitabine. However, other chemotherapies can be applied.

Some embodiments comprise treating a human subject whose HRG gene expression at an mRNA level is assessed as low or high with crizotinib. In some embodiments, the subject treated with crizotinib has an ALK gene rearrangement or fusion.

The invention is also directed to kits for facilitating an assessment of HRG gene expression at an mRNA level.

The invention is also directed to methods of identifying a human patient diagnosed with a locally advanced or metastatic non-small cell lung cancer (NSCLC) who is likely to benefit from a treatment comprising an anti-HER3 antibody comprising obtaining a biological sample from a human patient diagnosed with a locally advanced or metastatic NSCLC, using the sample, determining a value for HRG gene expression at an mRNA level in the human patient, and recording the value determined.

Some embodiments comprise receiving a biological sample from a human patient diagnosed with a locally advanced or metastatic NSCLC; using the sample, determining a value for HRG gene expression at an mRNA level in the human subject; and, optionally, recording the value determined.

Some embodiments comprise assessing if the value determined is below, at, or above a predetermined threshold value. In some embodiments, the predetermined threshold dCt value is in a range of from about 2.7 to about 4.1. In preferred embodiments, the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

Some embodiments involve characterizing the HRG gene expression at an mRNA level as high if the value determined is below the predetermined threshold value.

Some embodiments involve characterizing the HRG gene expression at an mRNA level as low if the value determined is at or above the predetermined threshold value.

Some embodiments comprise reporting the value determined to an attending physician or other medical practitioner.

In some embodiments, the sample comprises a cancer tissue sample.

In some embodiments, the subject does not harbor an epidermal growth factor receptor (EGFR) sensitizing mutation. In preferred embodiments, the subject harbors wild-type EGFR. In even more preferred embodiments, the subject has progressed on at least one prior systemic therapy. In more preferred embodiments, a tumor tissue or fragment thereof for or with which the HRG gene expression is assessed has been removed from the subject prior to any (systemic) therapy.

In some embodiments, the treatment comprises an anti-HER3 antibody in combination with one or more of (i) an EGFR inhibitor or a HER inhibitor, (ii) a chemotherapy, (iii) radiation, and (iv) an other targeted agent.

The invention is also directed to methods where HRG gene expression is assessed as high based on randomized clinical data.

The invention is also directed to methods of receiving or undergoing a treatment for a locally advanced or metastatic non-small cell lung cancer (NSCLC) tumor or abstaining therefrom. In some embodiments, the methods comprise providing an autologous tissue sample or consenting to a taking of same to facilitate an assessment of HRG gene expression at an mRNA level in a human subject diagnosed with a locally advanced or metastatic NSCLC; and receiving a treatment comprising an anti-HER3 antibody if HRG gene expression at an mRNA level is assessed as high, or abstaining from a treatment comprising an anti-HER3 antibody if HRG gene expression at an mRNA level is assessed as low.

The invention is also directed to methods of electing a treatment for a locally advanced or metastatic non-small cell lung cancer (NSCLC) tumor. In some embodiments, the methods comprise receiving an assessment of HRG gene expression at an mRNA level in a human subject diagnosed with a locally advanced or metastatic NSCLC; and electing to withhold a treatment comprising an anti-HER3 antibody if HRG gene expression at an mRNA level is assessed as low, or electing to administer a treatment comprising an anti-HER3 antibody if HRG gene expression at an mRNA level is assessed as high.

The present invention includes the following (1) to (97), but is not limited thereto.

(1) A method of treating a human subject harboring a locally advanced or metastatic non-small cell lung cancer (NSCLC) tumor comprising:
  assessing HRG gene expression at an mRNA level in a human subject diagnosed with a locally advanced or metastatic NSCLC; and
  administering a treatment comprising an anti-HER3 antibody to a human subject whose HRG gene expression at an mRNA level is assessed as high.

(2) The method of (1) in which the HRG gene expression at an mRNA level is assessed as high if a delta Ct (dCt) value is observed, which is below a predetermined threshold, from a biological sample taken from the subject diagnosed with a locally advanced or metastatic NSCLC.

(3) The method of (2) in which the predetermined threshold is chosen statistically to minimize undesirable effects of false positives and false negatives.

(4) The method of (2) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(5) The method of (1), wherein the subject harbors wild-type EGFR.

(6) The method of (5), wherein the tumor has progressed on at least one prior systemic therapy.

(7) The method of (1) in which HRG gene expression at an mRNA level is assessed using quantitative reverse transcriptase polymerase chain reaction (qRT-PCR), RNA sequencing or ISH.

(8) The method of (2) in which the biological sample comprises a tumor sample.

(9) The method of (1) in which the anti-HER3 antibody is selected from the group consisting of patritumab, duligotumab (MEHD-7945A), seribantumab (MM-121), MM-111, LJM716, RG-7116, tri-specific anti-EGFR/ERBB3 zybody, huHER3-8, or a derivative or fragment of any of these.

(10) The method of (1) in which the treatment comprises an anti-HER3 antibody in combination with one or more of (i) a HER inhibitor, (ii) a chemotherapy, (iii) radiation, and (iv) an other targeted agent.

(11) The method of (10), wherein the HER inhibitor is selected from the group consisting of trastuzumab, T-DM1, lapatinib, pertuzumab, cetuximab, panitumumab gefitinib, afatinib, dacomitinib, KD-019 and erlotinib.

(12) The method of (10), wherein the chemotherapy is selected from the group consisting of cisplatin, carboplatin, gemcitabine, pemetrexed, irinotecan, 5-fluoruracil, paclitaxel, docetaxel, and capecitabine.

(13) A method of treating a human subject harboring a locally advanced or metastatic non-small cell lung cancer (NSCLC) tumor comprising:
  assessing HRG gene expression at an mRNA level in a human subject diagnosed with a locally advanced or metastatic NSCLC; and
  withholding a treatment comprising an anti-HER3 antibody to a human subject whose HRG gene expression at an mRNA level is assessed as low.

(14) The method of (13) in which the HRG gene expression at an mRNA level is assessed as low if a delta Ct (dCt) value is observed, which is at or above a predetermined threshold, from a biological sample taken from the subject diagnosed with a locally advanced or metastatic NSCLC.

(15) The method of (14) in which the predetermined threshold is chosen statistically to minimize undesirable effects of false positives and false negatives.

(16) The method of (14) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(17) The method of (13), wherein the subject harbors wild-type EGFR.

(18) The method of (17), wherein the tumor has progressed on at least one prior systemic therapy.

(19) The method of (13) in which HRG gene expression at an mRNA level is assessed using quantitative reverse transcriptase polymerase chain reaction (qRT-PCR), RNA sequencing or ISH.

(20) The method of (14) in which the biological sample comprises a tumor sample.

(21) The method of (13) in which the treatment withheld comprises an anti-HER3 antibody in combination with one or more of (i) a HER inhibitor, (ii) a chemotherapy, (iii) radiation, and (iv) an other targeted agent.

(22) The method of (13) further comprising treating a human subject whose HRG gene expression at an mRNA level is assessed as low with a HER inhibitor selected from the group consisting of trastuzumab, T-DM1, lapatinib, pertuzumab, cetuximab, panitumumab gefitinib, afatinib, dacomitinib, KD-019 and erlotinib.

(23) The method of (13), further comprising treating a human subject whose HRG gene expression at an mRNA level is assessed as low with a chemotherapy selected from the group consisting of cisplatin, carboplatin, gemcitabine, pemetrexed, irinotecan, 5-fluoruracil, paclitaxel, docetaxel, and capecitabine.

(24) A kit for facilitating an assessment of HRG gene expression at an mRNA level.

(25) A method of identifying a human patient diagnosed with a locally advanced or metastatic non-small cell lung cancer (NSCLC) tumor who is likely to benefit from a treatment comprising an anti-HER3 antibody comprising:
obtaining a biological sample from a human patient diagnosed with a locally advanced or metastatic NSCLC;
using the sample, determining a value for HRG gene expression at an mRNA level in the human patient; and
recording the value determined.

(26) The method of (25) further comprising assessing if the value determined is below, at, or above a predetermined threshold value.

(27) The method of (26) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(28) The method of (26), further comprising characterizing the HRG gene expression at an mRNA level as high if the value determined is below the predetermined threshold value.

(29) The method of (26), further comprising characterizing the HRG gene expression at an mRNA level as low if the value determined is at or above the predetermined threshold value.

(30) The method of (25), further comprising reporting the value determined to an attending physician or other medical practitioner.

(31) The method of (25) in which the sample comprises a cancer tissue sample.

(32) The method of (25), wherein the subject does not harbor an epidermal growth factor receptor (EGFR) sensitizing mutation.

(33) The method of (25), wherein the subject harbors wild-type EGFR.

(34) The method of (33), wherein the tumor has progressed on at least one prior systemic therapy.

(35) The method of (25), wherein the treatment comprises an anti-HER3 antibody in combination with one or more of (i) a HER inhibitor, (ii) a chemotherapy, (iii) radiation, and (iv) an other targeted agent.

(36) The method of any of (1) to (35), wherein HRG gene expression is assessed as high based on randomized clinical data.

(37) The method of (1), wherein the predetermined threshold dCt value is in a range of from about 2.7 to about 4.1.

(38) The method of (13), wherein the predetermined threshold dCt value is in a range of from about 2.7 to about 4.1.

(39) The method of (26), wherein the the predetermined threshold dCt value is in a range of from about 2.7 to about 4.1.

(40) A method of receiving or undergoing a treatment for a locally advanced or metastatic non-small cell lung cancer (NSCLC) tumor or abstaining therefrom comprising:
providing an autologous tissue sample or consenting to a taking of same to facilitate an assessment of HRG gene expression at an mRNA level in a human subject diagnosed with a locally advanced or metastatic NSCLC; and
receiving or undergoing a treatment comprising an anti-HER3 antibody if HRG gene expression at an mRNA level is assessed as high, or
abstaining from a treatment comprising an anti-HER3 antibody if HRG gene expression at an mRNA level is assessed as low.

(41) A method of electing a treatment for a locally advanced or metastatic non-small cell lung cancer (NSCLC) tumor comprising:
receiving or undergoing an assessment of HRG gene expression at an mRNA level in a human subject diagnosed with a locally advanced or metastatic NSCLC; and
electing to withhold or abstain from a treatment comprising an anti-HER3 antibody if HRG gene expression at an mRNA level is assessed as low, or
electing to receive or undergo a treatment comprising an anti-HER3 antibody if HRG gene expression at an mRNA level is assessed as high.

(42) A method of identifying a human patient diagnosed with a locally advanced or metastatic non-small cell lung cancer (NSCLC) tumor who is likely to benefit from a treatment comprising an anti-HER3 antibody comprising:
receiving a biological sample from a human patient diagnosed with a locally advanced or metastatic NSCLC;
using the sample, determining a value for HRG gene expression at an mRNA level in the human subject; and
optionally, recording the value determined.

(43) A method of treating a human subject harboring a locally advanced or metastatic non-small cell lung cancer (NSCLC) tumor comprising:
ordering an assessment of HRG gene expression at an mRNA level in a human subject diagnosed with a locally advanced or metastatic NSCLC; and
administering a treatment comprising an anti-HER3 antibody to the human subject whose HRG gene expression at an mRNA level is assessed as high.

(44) A method of withholding a treatment of a human subject harboring a locally advanced or metastatic non-small cell lung cancer (NSCLC) tumor comprising:
ordering an assessment of an HRG gene expression at an mRNA level in a human subject diagnosed with a locally advanced or metastatic NSCLC; and
withholding a treatment comprising an anti-HER3 antibody to the human subject whose HRG gene expression at an mRNA level is assessed as low.

(45) A method of treating a human subject harboring a locally advanced or metastatic non-small cell lung cancer (NSCLC) tumor comprising administering a treatment comprising an anti-HER3 antibody to a human subject diagnosed with a locally advanced or metastatic NSCLC whose HRG gene expression at an mRNA level is assessed as high.

(46) The method of (45) in which the HRG gene expression at an mRNA level is assessed as high if a delta Ct (dCt) value is observed, which is below a predetermined threshold, from a biological sample taken from the subject diagnosed with a locally advanced or metastatic NSCLC.

(47) The method of (46) in which the predetermined threshold is chosen statistically to minimize undesirable effects of false positives and false negatives.

(48) The method of (46) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(49) The method of (45), wherein the subject harbors wild-type EGFR.

(50) The method of (49), wherein the tumor has progressed on at least one prior systemic therapy.

(51) The method of (45), further comprising assessing gene expression at an mRNA level in the human subject diagnosed with the locally advanced or metastatic NSCLC, wherein HRG gene expression at an mRNA level is assessed using quantitative reverse transcriptase polymerase chain reaction (qRT-PCR), RNA sequencing or ISH.

(52) The method of (46) in which the biological sample comprises a tumor sample.

(53) The method of (45) in which the anti-HER3 antibody is selected from the group consisting of patritumab, duligotumab (MEHD-7945A), seribantumab (MM-121), MM-111, LJM716, RG-7116, tri-specific anti-EGFR/ERBB3 zybody, huHER3-8, or a derivative or fragment of any of these.

(54) The method of (45) in which the treatment comprises administering an anti-HER3 antibody in combination with one or more of (i) a HER inhibitor, (ii) a chemotherapy, (iii) radiation, and (iv) an other targeted agent.

(55) The method of (54), wherein the HER inhibitor is selected from the group consisting of trastuzumab, T-DM1, lapatinib, pertuzumab, cetuximab, panitumumab gefitinib, afatinib, dacomitinib, KD-019 and erlotinib.

(56) The method of (55), wherein the chemotherapy is selected from the group consisting of cisplatin, carboplatin, gemcitabine, pemetrexed, irinotecan, 5-fluoruracil, paclitaxel, docetaxel, and capecitabine.

(57) A method of treating a human subject harboring a locally advanced or metastatic non-small cell lung cancer (NSCLC) tumor comprising:
withholding a treatment comprising an anti-HER3 antibody to a human subject diagnosed with a locally advanced or metastatic NSCLC whose HRG gene expression at an mRNA level is assessed as low.

(58) The method of (57) in which the HRG gene expression at an mRNA level is assessed as low if a delta Ct (dCt) value is observed, which is at or above a predetermined threshold, from a biological sample taken from the subject diagnosed with a locally advanced or metastatic NSCLC.

(59) The method of (58) in which the predetermined threshold is chosen statistically to minimize undesirable effects of false positives and false negatives.

(60) The method of (58) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(61) The method of (57), wherein the subject harbors wild-type EGFR.

(62) The method of (61), wherein the tumor has progressed on at least one prior systemic therapy.

(63) The method of (57), further comprising assessing HRG gene expression at an mRNA level in the human subject diagnosed with the locally advanced or metastatic NSCLC, wherein HRG gene expression at an mRNA level is assessed using quantitative reverse transcriptase polymerase chain reaction (qRT-PCR), RNA sequencing or ISH.

(64) The method of (58) in which the biological sample comprises a tumor sample.

(65) The method of (57) in which the treatment withheld comprises an anti-HER3 antibody in combination with one or more of (i) a HER inhibitor, (ii) a chemotherapy, (iii) radiation, and (iv) an other targeted agent.

(66) The method of (57) further comprising treating a human subject whose HRG gene expression at an mRNA level is assessed as low with a HER inhibitor selected from the group consisting of trastuzumab, T-DM1, lapatinib, pertuzumab, cetuximab, panitumumab gefitinib, afatinib, dacomitinib, KD-019 and erlotinib.

(67) The method of (57), further comprising treating a human subject whose HRG gene expression at an mRNA level is assessed as low with a chemotherapy selected from the group consisting of cisplatin, carboplatin, gemcitabine, pemetrexed, irinotecan, 5-fluoruracil, paclitaxel, docetaxel, and capecitabine.

(68) A kit for facilitating an assessment of HRG gene expression at an mRNA level.

(69) A method of identifying a human patient diagnosed with a locally advanced or metastatic non-small cell lung cancer (NSCLC) tumor who is likely to benefit from a treatment comprising an anti-HER3 antibody comprising:
obtaining a biological sample taken from a human patient diagnosed with a locally advanced or metastatic NSCLC;
using the sample, determining a value for HRG gene expression at an mRNA level in the human patient; and
optionally, recording the value determined.

(70) The method of (69) further comprising assessing if the value determined is below, at, or above a predetermined threshold value.

(71) The method of (70) in which the predetermined threshold dCt value is selected from the group consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0.

(72) The method of (70), further comprising characterizing the HRG gene expression at an mRNA level as high if the value determined is below the predetermined threshold value.

(73) The method of (70), further comprising characterizing the HRG gene expression at an mRNA level as low if the value determined is at or above the predetermined threshold value.

(74) The method of (69), further comprising reporting the value determined to an attending physician or other medical practitioner.

(75) The method of (69) in which the sample comprises a cancer tissue sample.

(76) The method of (69), wherein the subject does not harbor an epidermal growth factor receptor (EGFR) sensitizing mutation.

(77) The method of (69), wherein the subject harbors wild-type EGFR.

(78) The method of (77), wherein the tumor has progressed on at least one prior systemic therapy.

(79) The method of (69), wherein the treatment comprises an anti-HER3 antibody in combination with one or more of (i) a HER inhibitor, (ii) a chemotherapy, (iii) radiation, and (iv) an other targeted agent.

(80) The method of any of (1) to (79), wherein HRG gene expression is assessed as high based on randomized clinical data.

(81) The method of (46), wherein the predetermined threshold dCt value is in a range of from about 2.7 to about 4.1.

(82) The method of (58), wherein the predetermined threshold dCt value is in a range of from about 2.7 to about 4.1.

(83) The method of (70), wherein the the predetermined threshold dCt value is in a range of from about 2.7 to about 4.1.

(84) A method of any of the preceding claims, wherein HRG gene expression is assessed using an regulatory authority-approved test.

(85) The method of (84), wherein the regulatory authority-approved test is an FDA (Food and Drug Administration, the United States)-approved, EMA (European Medicines Agency, European Union)-approved or PMDA (Pharmaceuticals and Medical Devices Agency, Japan)-approved test.

(86) The method of (2) in which the predetermined threshold dCt value is selected from the group consisting of 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 and −7.3.

(87) The method of (14) in which the predetermined threshold dCt value is selected from the group consisting of 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0, 1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 and −7.3.

(88) The method of (26) in which the predetermined threshold dCt value is selected from the group consisting of 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0, 1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 and −7.3.

(89) The method of (6) in which a tumor tissue or fragment thereof for or with which the HRG gene expression is assessed has been removed from the subject prior to any therapy.

(90) The method of (18) in which a tumor tissue or fragment thereof for or with which the HRG gene expression is assessed has been removed from the subject prior to any therapy.

(91) The method of (34) in which a tumor tissue or fragment thereof for or with which the HRG gene expression is assessed has been removed from the subject prior to any therapy.

(92) The method of (2) in which the predetermined threshold dCt value is in a range of from about −7.3 to about 5.0.

(93) The method of (14) in which the predetermined threshold dCt value is in a range of from about −7.3 to about 5.0.

(94) The method of (26) in which the predetermined threshold dCt value is in a range of from about −7.3 to about 5.0.

(95) The method of (50) in which a tumor tissue or fragment thereof for or with which the HRG gene expression is assessed has been removed from the subject prior to any therapy.

(96) The method of (62) in which a tumor tissue or fragment thereof for or with which the HRG gene expression is assessed has been removed from the subject prior to any therapy.

(97) The method of (78) in which a tumor tissue or fragment thereof for or with which the HRG gene expression is assessed has been removed from the subject prior to any therapy.

DETAILED DESCRIPTION OF THE INVENTION

Definitions

Figure 1:
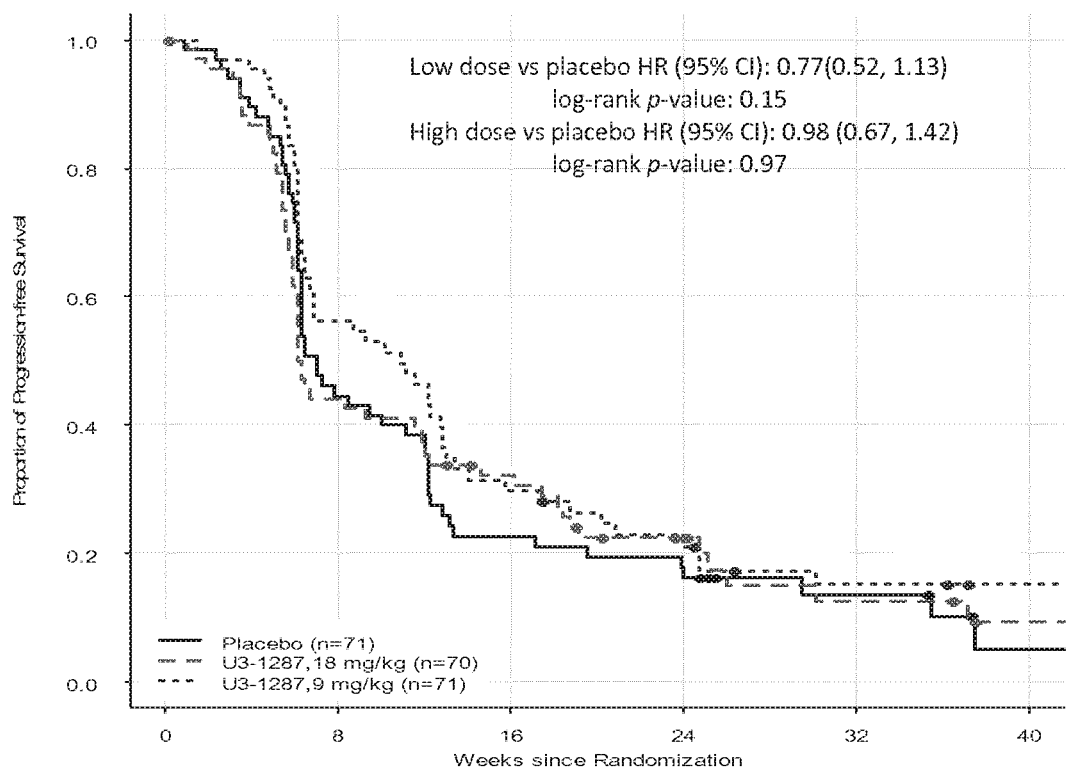
FIG. 1 depicts progression-free survival (showing high- and low-dose patritumab+erlotinib vs. placebo+erlitonib) for all subjects from the study in Example 2.

As used herein, unless indicated otherwise, when referring to a numerical value, the term "about" means plus or minus 10% of the enumerated value.

As used herein, "cancer" and "tumor" are interchangeable.

As used herein, "treatment" means a medical care given to a subject or patient, or administration of a dose of a medicine. In some embodiments, "treatment" could be "pharmaceutical composition", "medicament" or "agent" that could comprise a HER inhibitor such as anti-HER3 antibody. In some embodiments, "treatment" could be a "chemotherapy", "immune therapy", "immunotherapy" or "radiotherapy".

As used herein, "EGFR mutation" means any mutation in an EGFR gene. "EGFR mutation" can be, for example, an EGFR exon 19 deletion and/or an exon 21 (L858R) substitution mutation. However, "EGFR mutation" is not limited thereto.

As used herein, "HER" is one selected from the group consisting of HER1 (EGFR), HER2, HER3 and HER4.

As used herein, "HER3" means the human protein encoded by the gene identified by Entrez Gene ID No. 2065, and allelic variants thereof.

As used herein, "HER inhibitor" means a molecule (small molecule or macromolecule, e.g., an antibody or antigen binding fragment thereof) that inhibits, neutralizes, prevents or eliminates at least a portion of the biological activity of a HER. Preferably, a HER inhibitor binds to the HER. However, "HER inhibitor" can be a molecule that does not directly bind to the HER, as long as said molecule inhibits, neutralizes, prevents or eliminates at least a portion of the biological activity of the HER. Examples of HER1 inhibitors (EGFR inhibitor) include lapatinib, erlotinib, cetuximab, gefitinib, afatinib, dacomitinib, panitumumab and KD-019. Examples of HER2 inhibitors include trastuzumab, pertuzumab and trastuzumab emtansine (T-DM1).

As used herein, "HER3 inhibitor" means a molecule (small molecule or macromolecule, e.g., an antibody or antigen binding fragment thereof) that inhibits, neutralizes, prevents or eliminates at least a portion of the biological activity of HER3. Preferably, the HER3 inhibitor binds to HER3. However, "HER3 inhibitor" can be a molecule that does not directly bind to HER3, as long as said molecule inhibits, neutralizes, prevents or eliminates at least a portion of the biological activity of HER3. The effect on "biological activity" can be direct or indirect, such as downstream signal transduction and heterodimerization with other HER family molecules such as EGFR, HER2 and HER4. For example, the HER3 inhibitor can be an inhibitor of EGFR/HER3, HER2/HER3 or HER4/HER3 heterodimerization, or an inhibitor of a signal transduction derived from any of these heterodimerizations. In this context, "HER3 inhibitor" can include, for example pertuzumab, nimotuzumab, MM-111 and cetuximab. Further, without being bound by theory it is believed that HER3 forms a heterodimer with non-HER receptors, such as MET (c-MET). Thus, in some embodiments "HER3 inhibitor" can include, for example, a MET inhibitor such as onartuzumab and/or tivantinive.

As used herein, "HRG" (also known as neuregulin-1, NRG1, heregulin, and HRG1) means the human protein encoded by the gene identified by Entrez Gene ID No. 3084, and allelic variants thereof.

As used herein, "non-small cell lung cancer" and "non-small cell lung carcinoma" are interchangeable.

As used herein, "predetermined threshold (value)" means the threshold numeric value at which a classifier gives the desirable balance between (the cost of) false negatives and false positives.

Preferably, "predetermined threshold (value)" means the potential threshold numeric value to divide the entire population (of patients or subjects) into two (or more) subgroups so that it can bring clinical benefit to patients with the threshold or higher (HRG) gene expression (used herein as "high HRG" subgroup), compared to patients with the lower (HRG) gene expression than the threshold (used herein as "low HRG" subgroup).

In case a threshold value is a dCt, preferably, "predetermined threshold (value)" means the potential threshold numeric value to divide the entire population (of patients or subjects) into two (or more) subgroups so that it can bring clinical benefit to patients with the threshold or lower (HRG) gene expression (used herein as "high HRG" subgroup), compared to patients with the higher (HRG) gene expression than the threshold (used herein as "low HRG" subgroup).

In some embodiments, "predetermined threshold" is statistically (and clinically) determined, refined, adjusted and/or confirmed through, on, or based on, a clinical study and analyses of outcome thereof (collectively, "clinical data"), and/or a preclinical or non-clinical study (collectively, "non-clinical data"), in order to minimize undesirable effects of false positives and false negatives.

In some embodiments, "predetermined threshold" is statistically (and clinically) determined, refined, adjusted and/or confirmed on, or based on, clinical data (and optionally non-clinical data), further more preferably randomized clinical data (and optionally non-clinical data), to ensure all patients that benefit from treatment are included in the HRG high subgroup.

More preferably, "predetermined threshold" is determined, refined, adjusted and/or confirmed through, on, or based on pharmacological characteristics (i.e., mechanism of action), preclinical or non-clinical study data, clinical study data, and commercial sample data purchased from external companies or the like, in order to maximize clinical benefit from "high HRG" subgroup compared with "low HRG" subgroup. Some statistical method such as Adaptive Biomarker Threshold Design (i.e., maximum likelihood approach), Jiang W, Freidlin B, Simon R. Biomarker-Adaptive Threshold Design: A Procedure for Evaluating Treatment With Possible Biomarker-Defined Subset Effect, J Natl Cancer Inst. 2007; 99(13): 1036-43, and the like is used to determine, refine, adjust and/or confirm the threshold using the all available data of pre/non-clinical studies, clinical studies, commercial sample, etc. (to ensure all patients that benefit from treatment are included in the HRG high subgroup). In some embodiments, "predetermined threshold" is determined so that high HRG subgroup can be larger or can include all patients that drive benefit from treatment.

As used herein, "subject," "human subject," and "patient" are interchangeable.

As used herein, "subject suffering from a cancer" and "subject harboring a cancer" are interchangeable.

In some preferred embodiments, when a group of patients suffering from a cancer are treated by administering a HER3 inhibitor or placebo with or without a further medicament, and said group is divided into "high HRG" subgroup and "low HRG" subgroup using the predetermined threshold, average anti-cancer efficacy of the administered HER3 inhibitor is better than that of control (e.g. placebo) with clinical(ly) (meaningful) benefit in the "high HRG" subgroup, while average anti-cancer efficacy of the administered HER3 inhibitor is slightly better or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinical(ly) (meaningful) benefit in "high HRG" subgroup, while average anti-cancer efficacy of the administered HER3 inhibitor is not statistically significantly better than that of control (e.g. placebo) with no clinical(ly) (meaningful) benefit in the "low HRG" subgroup.

In other preferred embodiments, when a group of patients suffering from a cancer is divided into a "high HRG" subgroup and a "low HRG" subgroup using the predetermined threshold, and each group is treated by administering a HER3 inhibitor or placebo with or without a further medicament, average anti-cancer efficacy of the administered HER3 inhibitor is better than that of a control (e.g. placebo) with clinical(ly) (meaningful) benefit in the "high HRG" subgroup, while average anti-cancer efficacy of the administered HER3 inhibitor is slightly better or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup, while average anti-cancer efficacy of the administered HER3 inhibitor is not statistically significantly better than that of control (e.g. placebo) with no clinical(ly) (meaningful) benefit in the "low HRG" subgroup.

In other embodiments, "predetermined threshold" can be the median of HRG levels which are measured in pre-/non-clinical study, clinical study and/or commercial sample, for example with a group of patients suffering from a cancer whose HRG levels are measurable (can be measured) or detectable. In other preferred embodiments, when a group of patients suffering from a cancer, such as non-small cell lung cancer (NSCLC), are treated by administering a HER3 inhibitor or placebo with or without a further medicament, and the group is divided into a high HRG subgroup and low HRG subgroup using the median HRG level of the patients as the predetermined threshold, average anti-cancer efficacy of the administered HER3 inhibitor is better than that of control (e.g. placebo) with clinical(ly) (meaningful) benefit in the "high HRG" subgroup, while average anti-cancer efficacy of the administered HER3 inhibitor is slightly better or not better than that of control (e.g. placebo) with no clinical(ly) (meaningful) benefit in the "low HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup, while average anti-cancer efficacy of the administered HER3 inhibitor is not statistically significantly better than that of control (e.g. placebo) with no clinical(ly) (meaningful) benefit in the "low HRG" subgroup. In some embodiments, the predetermined threshold is the median of HRG level of a group of patients suffering from a cancer, and said threshold can be refined or adjusted, (to ensure all patients that benefit from treatment are included in the HRG high sub group).

In other preferred embodiments, when a group of patients suffering from a cancer is divided into a "high HRG" subgroup and "low HRG" subgroup using the predetermined threshold, and the "high HRG" subgroup is treated by administering a HER3 inhibitor or placebo with or without a further medicament, average anti-cancer efficacy of the administered HER3 inhibitor is better than that of a control (e.g. placebo) with clinical(ly) (meaningful) benefit in the "high HRG" subgroup. In more preferred embodiments, average anti-cancer efficacy of the administered HER3 inhibitor is statistically significantly better than that of control (e.g. placebo) with clinical(ly) (meaningful) benefit in the "high HRG" subgroup.

In other preferred embodiments, when "high HRG" patients suffering from a cancer are identified using the predetermined threshold, and the patients are treated by administering a HER3 inhibitor or placebo with or without a further medicament, average anti-cancer efficacy of the administered HER3 inhibitor is better than that of a control (e.g. placebo) with clinical(ly) (meaningful) benefit. In more preferred embodiments, average anti-cancer efficacy of the administered HER3 inhibitor is statistically significantly better than that of control (e.g. placebo) with clinical(ly) (meaningful) benefit.

As used herein, "further medicament" means any therapeutic or prophylactic molecule other than the HER3 inhibitor which is to be used in combination with said molecule. In some embodiments, "further medicament" is one or more of a HER inhibitor, a chemotherapy, or a radiation therapy.

In some embodiments, an indicator (index) of "anti-cancer efficacy" can be progression-free survival (PFS) or overall survival (OS), but is not limited thereto. The indicator can be any surrogate marker of anti-cancer efficacy of a HER3 inhibitor.

As used herein, "high HRG" is a numerical value representing, or represents, a level of HRG gene expression at or above a predetermined threshold. In the present invention, "high HRG", "high HRG (sub)group" and "high HRG patient (or subject)" mean a level of HRG gene expression at or above a (predetermined) threshold, (sub)group having level(s) of HRG gene expression at or above a (predetermined) threshold, and, patient (or subject) having a level of HRG gene expression at or above a (predetermined) threshold, respectively. The HRG classification can be based on HRG gene expression at an RNA level, for example.

As used herein, "low HRG" is a numerical value representing, or represents, a level of HRG gene expression at or below a predetermined threshold. In the present invention, "low HRG", "low HRG (sub)group" and "low HRG patient (or subject)" mean a level of HRG gene expression at or below a (predetermined) threshold, (sub)group having level(s) of HRG gene expression at or below a (predetermined) threshold, and, patient (or subject) having a level of HRG gene expression at or below a (predetermined) threshold, respectively. The HRG classification can be based on HRG gene expression at an RNA level, for example.

As used herein, "response" or "responding" to treatment means, with regard to a treated tumor, that the tumor displays: (a) slowing of growth, (b) cessation of growth, or (c) regression.

The methods disclosed herein can be used for identifying a subject, for example a human subject, harboring or diagnosed with a tumor or cancer cells. In some embodiments, the subject harbors solid or liquid tumors that may be driven by the HER3 pathway, or that may have resistance to other therapies mediated by the HER3 pathway. In some embodiments, the subject harbors lung cancer, colorectal cancer, head and neck cancer, breast cancer, gastrointestinal cancer, pancreatic cancer, prostate cancer, ovarian cancer, endometrial cancer, salivary gland cancer, renal cancer, colon cancer, gastric cancer (stomach cancer), thyroid cancer, bladder cancer, glioma, melanoma, metastatic breast cancer, epidermal carcinoma, esophageal cancer, cervical cancer, squamous cell carcinoma, small-cell lung cancer, or non-small cell lung cancer.

In some embodiments, the methods disclosed herein can be used to identify a subject harboring a locally advanced or metastatic tumor, such as a locally advanced or metastatic NSCLC (tumor) or locally advanced or metastatic head and neck cancer. In some embodiments, methods disclosed herein can be used to identify a subject, such as a subject harboring a locally advanced or metastatic NSCLC (tumor), that is likely to benefit from a treatment comprising an anti-HER3 antibody or HER3 inhibitor having a low molecular weight. In some embodiments, the subject is harboring a Stage III, e.g., Stage IIIb, or Stage IV tumor. Methods of identifying a subject can comprise, for example, assessing HRG gene expression at an mRNA level in a human subject diagnosed with a tumor or cancer.

In some embodiments, methods disclosed herein can be used to identify a subject harboring a locally advanced or metastatic NSCLC (tumor), that is likely to benefit from a treatment comprising (administering) an anti-HER3 antibody or HER3 inhibitor having a low molecular weight, provided that, any subject who having an ALK gene fusion or rearrangement is excluded from those to whom the methods are applied.

In some embodiments, the methods disclosed herein can be used to treat a subject identified as harboring a tumor or cancer cells. In some embodiments, methods of identifying or treating a human subject harboring a locally advanced or metastatic NSCLC (tumor) can comprise assessing HRG gene expression at an mRNA level in a human subject diagnosed with a locally advanced or metastatic NSCLC. In some embodiments, the subject does not harbor an epidermal growth factor receptor (EGFR) sensitizing mutation. In some embodiments, the subject harbors wild-type EGFR. In some embodiments, the subject does not harbor an ALK gene fusion or rearrangement. In some embodiments, the disease or tumor has progressed on at least one prior systemic therapy, such as chemotherapy. Some embodiments comprise administering a treatment comprising an anti-HER3 antibody to a human subject whose HRG gene expression at an mRNA is assessed as high. In some embodiments, treatment comprises (administering) an anti-HER3 antibody in combination with at least one agent that inhibits a HER family receptor other than HER3. In some embodiments, treatment comprises (administering) an anti-HER3 antibody in combination with at least one agent that inhibits a non-HER family tyrosine kinase receptor. In some embodiments, an anti-HER3 antibody is administered in combination with non-specific chemotherapy.

In some preferred embodiments, patients to whom the methods disclosed herein can be applied are heregulin high, EGFR wild-type subjects with locally advanced or metastatic non-small cell lung cancer who have progressed on at least one prior systemic therapy. In some embodiments, the patients are HER inhibitor naïve. In preferred embodiments, a tumor tissue or fragment thereof for or with which the HRG gene expression is assessed has been removed from the subject or patient prior to any (systemic) therapy.

In some preferred embodiments, patients to whom the methods disclosed herein can be applied include a subject with a first-line metastatic or locally advanced head and neck cancer that will be concurrently treated with one or more of cetuximab, cisplatin, panitumumab, 5-fluoruracil, radiotherapy, and radiation therapy (locally advanced only).

In some embodiments, patients to whom the methods disclosed herein can be applied include a subject with a second-line metastatic NSCLC or other cancer that will be concurrently treated with docataxel.

In some embodiments, patients to whom the methods disclosed herein can be applied include a subject with a NSCLC or other cancer that will be concurrently treated with an immune therapy.

In some embodiments, patients to whom the methods disclosed herein can be applied include a subject with a third line, HER2 positive, (metastatic) breast cancer that will be concurrently treated with a PI3K pathway inhibitor.

In some embodiments, patients to whom the methods disclosed herein can be applied include a subject with HER2 negative (metastatic) breast cancer that will be concurrently treated with a hormone therapy or PI3K pathway inhibitor.

In the present invention, PI3K pathway inhibitors include PI3K inhibitors, mTOR inhibitors and AKT inhibitors.

In some embodiments, patients to whom the methods disclosed herein can be applied include a subject with a first-line metastatic EGFR-sensitizing mutant positive for NSCLC or other cancer that will be concurrently treated with one or more of erlotinib, gefitinib, and afitinib.

In some embodiments, patients to whom the methods disclosed herein can be applied include a subject with a first-line metastatic NSCLC or other cancer that will be concurrently treated with platinum-based chemotherapy.

In some embodiments, patients to whom the methods disclosed herein can be applied include a subject with RAS wild-type colorectal cancer that will be concurrently treated with one or more of cetuximab, panitumumab, and chemotherapy.

In some embodiments, patients to whom the methods disclosed herein can be applied include a subject that with HER2 positive first line metastatic breast cancer or other cancer that will be concurrently treated with one or more of trastuzumab, paclitaxel, docataxel, T-DM1 and pertuzumab.

In some embodiments, patients to whom the methods disclosed herein can be applied include a subject that with HER2 positive second or later line metastatic breast cancer or other cancer that will be concurrently treated with one or more of lapatinib, capecitabine, trastuzumab, and paclitaxel.

In some embodiments, patients to whom the methods disclosed herein can be applied have not failed with an earlier line of therapy. In some embodiments, patients to whom the methods disclosed herein can be applied have not failed with an earlier line of therapy and the patients have been classified as "high HRG."

In some embodiments, the methods disclosed herein can be used to identify and/or treat HRG high, EGFR wild-type subjects with locally advanced or metastatic NSCLC who will benefit from treatment of patritumab in combination with a HER inhibitor.

In some embodiments, the methods disclosed herein can be used to identify and/or treat HRG high, EGFR wild-type subjects with locally advanced or metastatic NSCLC who will benefit from treatment of patritumab in combination with chemotherapy.

In some embodiments, the methods disclosed herein can be used to identify and/or treat HRG high, EGFR mutated subjects, for example subjects with locally advanced or metastatic NSCLC who will benefit from treatment of patritumab in combination with a HER inhibitor.

In some embodiments, the methods disclosed herein can be used to identify and/or treat HRG high, EGFR mutated subjects with locally advanced or metastatic NSCLC who will benefit from treatment of patritumab in combination with chemotherapy.

In some embodiments, the methods disclosed herein can be used to identify and/or treat a "HRG high" patient suffering from a cancer who will benefit from treatment of patritumab in combination with an immune therapy or immunotherapy. Such cancers include NSCLC.

In some embodiments, the methods disclosed herein can be used to identify and/or treat a "HRG high" patient suffering from a cancer who will benefit from treatment of patritumab in combination with a hormone therapy or PI3K (phosphoinositide 3-kinase) pathway inhibitor.

Such cancers include breast cancer, preferably, HER2-negative breast cancer. Such PI3K pathway inhibitors include PI3K inhibitors, AKT inhibitors and mTOR (mammalian Target Of Rapamycin) inhibitors.

In some embodiments, the methods disclosed herein can be used to identify and/or treat a "HRG high" patient suffering from a cancer who will benefit from treatment of patritumab in combination with a PI3K inhibitor. Such cancers include breast cancer, preferably, HER2-positive breast cancer.

In some embodiments, the methods disclosed herein can be used to identify and/or treat a "HRG high" patient suffering from a cancer who will benefit from treatment of patritumab in combination with a ALK inhibitor. Such cancers include NSCLC. Such ALK (anaplastic lymphoma kinase) inhibitor includes crizotinib (Xalkori).

In some embodiments, the methods disclosed herein can be used to identify and/or treat acute respiratory distress syndrome, pulmonary fibrosis, schizophrenia, heart disease, atherosclerosis, and Duchenne's muscular dystrophy.

HER3 Antibodies

Antibodies suitable for treatment are not particularly limited, and can be any protein or ligand that can bind to HER3. In some embodiments, the antibodies can be binding proteins or fragments thereof that bind to HER3. In some preferred embodiments, the antibodies can inhibit, neutralize, prevent or eliminate at least a portion of the biological activity of HER3.

HER3 antibodies can be, for example, one or more of patritumab, duligotumab (MEHD-7945A), seribantumab (MM-121), MM-111, LJM716, RG-7116 (glycoengineered anti-HER3 monoclonal antibody), tri-specific anti-EGFR/ERBB3 zybody, huHER3-8, or a derivative or fragment of any of these that can bind to HER3.

Antibody fragments include, for example, Fab fragments, Fab' fragments, F(ab')$_2$ fragments, Fv fragments, diabodies (Hollinger et al. (1993) *Proc. Natl. Acad. Sci. U.S.A.* 90:6444-6448), single chain antibody molecules (Plückthun in: *The Pharmacology of Monoclonal Antibodies* 113, Rosenburg and Moore, eds., Springer Verlag, N.Y. (1994), 269-315), scFv fragments, and other fragments that can inhibit HER3.

Derivatives of antibodies or antibody fragments can include, for example, a bispecific antibody, a multispecific antibody, a biscFv fragment, a diabody, a nanobody, an antibody-drug conjugate, an immunotoxin, and/or an immunocytokine, but are not limited thereto.

Further examples of suitable antibodies can be found, for example, in U.S. Pat. No. 7,705,130, which is herein incorporated by reference in its entirety.

According to the present invention, an isolated binding protein that is capable of binding to HER3 interacts with at least one epitope in the extracellular part of HER3. The epitopes are preferably located in domain L1, which is the amino terminal domain, in domain S1 and S2, which are the two Cysteine-rich domains, or in domain L2, which is flanked by the two Cysteine-rich domains. The epitopes may also be located in combinations of domains such as but not limited to an epitope comprised by parts of L1 and S1.

Biological Sample

A biological sample taken from a subject, such as a subject diagnosed with a locally advanced or metastatic NSCLC, can be used as a source of RNA, so the level of HRG gene expression at the RNA level in the sample can be determined. The biological sample can comprise, for example, blood, e.g., whole blood or blood derivatives including exosomes, tissue, cells, and/or circulating tumor cells. In some embodiments, the biological sample can be taken from a tumor.

The biological sample can be obtained by any known methods, such as venipuncture or with conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tumor samples. The biological sample should be large enough to provide sufficient RNA or thin sections for measuring HRG gene expression.

In some embodiments, the methods described herein comprise providing an autologous tissue sample or consenting to the taking of an autologous tissue sample, e.g., to facilitate an assessment of HRG gene expression at an mRNA level in a human subject diagnosed with a locally advanced or metastatic NSCLC.

The biological sample can be in any form that allows measurement of HRG expression or content. In other words, the sample must be sufficient for RNA extraction or preparation of thin sections. Accordingly, the sample can be fresh, preserved through suitable cryogenic techniques, or preserved through non-cryogenic techniques. For example, a standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

HRG Gene Expression

As described herein, determining or measuring the level of HRG gene expression in a biological sample can be performed by any suitable method. Several such methods are known in the art. For example, determining HRG gene expression can be done by measuring the level or amount of HRG RNA, e.g., mRNA, in a sample.

HRG gene expression can be detected by any known methods. For example, primers can be designed to cover the EGF-like domain and/or Neuregulin domain of HRG isoforms. These primers can be based on sequences commonly found on mRNA of, for example, HRG-α, HRG-β1, HRG-β1b, HRG-β1c, HRG-β1d, HRG-β2, HRG-β2b, ndf43, ndf43b and/or ndf43c.

For example, gene expression can be measured by using a TaqMan probe (Life Technologies Corporation; code Hs01101537_m1) to amplify and detect a nucleotide sequence consisting of total 72 nucleotides in GenBank Accession No. NM_013964.3. The center/middle of the amplified nucleotide sequence can be located at the $1318^{th}$ nucleotide of the NM_013964.3. The amplified sequence can be one that is commonly found on mRNA of HRG-α, HRG-β1, HRG-β1b, HRG-β1c, HRG-β1d, HRG-β2, HRG-β2b, ndf43, ndf43b and/or ndf43c.

The nucleotide sequence can consist of the nucleotides No, 1221 to 1780 of the NM_013964.3 that is commonly found on mRNA of HRG variants. Therefore, the primers and/or probe for detecting HRG can be designed to amplify full-length or any partial sequence of the nucleotides No. 1221 to 1780 of the NM_013964.3.

The primers and/or probes of PCR or microarray can be designed on the 3' end of mRNA because, without being bound by theory, it is believed to lead to higher preservation (stability) through experimental procedures like RNA isolation or cDNA synthesis. In some embodiments, the probes can be designed based on a sequence of interest to detect particular form of transcript variant.

Non-limiting examples of suitable detection methods are described below.

RNA Analysis

Conventional microarray analysis and quantitative polymerase chain reaction (PCR) are examples of methods for determining the level of HRG gene expression at the mRNA level. In some embodiments, RNA is extracted from the cells, tumor or tissue of interest using standard protocols. In other embodiments, RNA analysis is performed using techniques that do not require RNA isolation.

Methods for rapid and efficient extraction of eukaryotic mRNA, i.e., poly(a) RNA, from tissue samples are well established and known to those of skill in the art. See, e.g., Ausubel et al, 1997, Current Protocols of Molecular Biology, John Wiley & Sons. The tissue sample can be fresh, frozen or fixed paraffin-embedded (FFPE) samples such as clinical study tumor specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al, 2001, BMC Genomics 8:279. Also see, De Andres et al, 1995, Biotechniques 18:42044; and Baker et al, U.S. Patent Application Publication No. 2005/0095634.

The use of commercially available kits with vendor's instructions for RNA extraction and preparation is widespread and common. Commercial vendors of various RNA isolation products and complete kits include Qiagen (Valencia, CA), Invitrogen (Carlsbad, CA), Ambion (Austin, TX) and Exiqon (Woburn, MA).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater® (Ambion, Austin, TX).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored under RNase-free conditions. Methods for stable storage of isolated RNA are known in the art. Various commercial products for stable storage of RNA are available.

Microarray

The mRNA expression level of HRG can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or any other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure HRG, plus necessary controls or standards, e.g., for data normalization, can be used in practicing the disclosed methods.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing disclosed methods, a person of ordinary skill in the art can use microarray technology to measure expression levels of genes encoding biomarker proteins without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, CA) and Affymetrix (Santa Clara, CA), but other array systems can be used.

Quantitative PCR

The level of mRNA encoding HRG can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial instruments and reagents for qRT-PCR (e.g., Qiagen (Valencia, CA) and Ambion (Austin, TX)).

Instruments and systems for automated performance of qRT-PCR are commercially available and used routinely in many laboratories. An example of a well-known commercial system is the Applied Biosystems 7900HT Fast Real-Time PCR System (Applied Biosystems, Foster City, CA).

Once mRNA is isolated, the first step in gene expression measurement by RT-PCR is the reverse transcription of the mRNA template into cDNA, which is then exponentially amplified in a PCR reaction. Two commonly used reverse transcriptases are avian myeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, MA). The resulting cDNA product can be used as a template in the subsequent polymerase chain reaction.

The PCR step is carried out using a thermostable DNA-dependent DNA polymerase. The polymerase most commonly used in PCR systems is a *Thermus aquaticus* (Taq) polymerase. The selectivity of PCR results from the use of primers that are complementary to the DNA region targeted for amplification, i.e., regions of the cDNAs reverse transcribed from genes encoding proteins of interest. Therefore, when qRT-PCR is employed in the present invention, primers specific to each marker gene are based on the cDNA sequence of the gene. Commercial technologies such as SYBR® green or TaqMan® (Applied Biosystems, Foster City, CA) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression of HRG genes can be designed and synthesized by one of skill in the art, without undue experimentation.

Alternatively, PCR primer sets for practicing the present invention can be purchased from commercial sources, e.g., Applied Biosystems. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene, including HRG.

qNPA™

In some embodiments, RNA analysis is performed using a technology that does not involve RNA extraction or isolation. One such technology is quantitative nuclease protection assay, which is commercially available under the name qNPA™ (High Throughput Genomics, Inc., Tucson, AZ). This technology can be advantageous when the tumor tissue samples to be analyzed are in the form of FFPE material. See, e.g., Roberts et al, 2007, Laboratory Investigation 87:979-997.

Nanostring

In some embodiments, RNA analysis is performed using nanostring technology. Methods of Nanostring use labeled reporter molecules, referred to as labeled "nanoreporters," that are capable of binding individual target molecules. Through the nanoreporters' label codes, the binding of the nanoreporters to target molecules results in the identification of the target molecules. Methods of Nanostring are described in U.S. Pat. No. 7,473,767.

Assessing HRG Gene Expression

HRG gene expression can be assessed in a biological sample from a human patient, such as a biological sample obtained from, taken from, or received from a human patient. Some embodiments comprise ordering or receiving an assessment of HRG gene expression at an mRNA level. Some embodiments comprise determining a value for HRG gene expression at an mRNA level and, optionally, recording the value determined.

HRG Gene Expression levels can be interpreted with respect to a predetermined threshold. An HRG gene expression level that is equal to or higher than the threshold score can be interpreted as predictive of the likelihood that a subject would respond to treatment with a HER3 inhibitor, e.g., an anti-HER3 antibody. In some embodiments, HRG gene expression levels lower than the threshold score can be interpreted as predictive of a tumor being resistant (non-responsive) to treatment with a HER3 inhibitor.

In some embodiments, HRG gene expression can be assessed as "high HRG" or "low HRG" based on a numerical value representing the level of HRG gene expression in a biological sample. A subject can be assessed as high HRG or low HRG based on, for example, HRG expression at a mRNA level.

The expression level can be assessed by any known methods, such as those described above. For example, an HRG assessment can be based on Ct value from a qRT-PCR assay. In some embodiments, HRG assessment can be based on the expression of additional genes that serve as controls or standards, e.g., for data normalization, or may be otherwise informative.

In some embodiments, HRG expression at an mRNA level is assessed using a regulatory authority-approved test. In some embodiments, the regulatory authority-approved test is an FDA-approved test, an EMA-approved test, or a JPMA-approved test.

Ct value and HRG gene expression are inversely related. Therefore, a lower Ct value translates to higher HRG gene expression. In some embodiments, HRG expression is assessed as high HRG if a delta Ct (dCt) value is observed that is below a predetermined threshold. The predetermined threshold can be chosen statistically to minimize undesirable effects of false positives and false negatives and can be, for example, about more than 20, 20, 19, 18, 17, 16, 15, 14, 13, 12, 11, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0, 1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2, −7.3, −7.4, −7.5, −7.6, −7.7, −7.8, −7.9, −8.0, −8.1, −8.2, −8.3, −8.4, −8.5, −8.6, −8.7, −8.8, −8.9, −9.0, −9.1, −9.2, −9.3, −9.4, −9.5, −9.6, −9.7, −9.8, −9.9, −10.0, −11, −12, −13, −14, −15, −16, −17, −18, −19, −20, −21, −22, −23, −24, −25, −26, −27, −28, −29, −30, −35, −40, −45, −50, −60, −70, −80, −90, −100 or less. In some embodiments, HRG expression can be assessed as "high HRG" if the dCt value is less than about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0, 1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 or −7.3. In some embodiments, HRG expression is assessed as "low HRG" if the dCt values is equal to or more than about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0, 1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 or −7.3. In some embodiments, the predetermined threshold is between about −20 and about 20, about −10 and about 10, about −7.3 and about 7.3, about −7.3 to 5.0, about 2.0 and about 5.0, about 2.7 and about 4.1, about 3.0 to about 4.1, about 3.0 to about 4.0, about 3.0 to about 3.9, about 3.4 to about 4.1, about 3.5 to about 4.0, about 3.5 to about 3.9, about 3.6 to about 3.9, about 3.5 to about 4.2, about 3.5 to about 4.5, about 3.6 to about 4.4, or about 3.5 to about 5.0. In some embodiments, the predetermined threshold can be a continuum.

In some embodiments, the predetermined threshold is set, for example at 3.9, so that 50% of the patient population is "high HRG." In some embodiments, the predetermined threshold is set, for example at 3.7, so that 48% of the patient population is "high HRG." In some embodiments, the predetermined threshold is set, for example at 3.5, so that 45% of the patient population is "high HRG." In some embodiments, the predetermined threshold is set, for example at 3.3, so that 40% of the patient population is "high HRG." In some embodiments, the predetermined threshold is set, for example at 3.0, so that 33% of the patient population is "high HRG." In some embodiments, the predetermined threshold is set, for example at 2.7, so that 25% of the patient population is "high HRG."

In some embodiments, higher HRG gene expression is correlated with better hazard ratios and p-values.

Treatment

In some embodiments, the subject can be treated by administering a treatment comprising an anti-HER3 antibody to a subject suffering from a cancer or other disease with HRG gene expression assessed as high. In some embodiments, the subject can be treated by withholding a treatment comprising an anti-HER3 antibody from a subject suffering from a cancer or other disease with HRG gene expression assessed as low.

In some embodiments, the subject can be treated by receiving or undergoing a treatment comprising an anti-HER3 antibody if HRG gene expression at an mRNA level is assessed as high or abstaining from a treatment comprising an anti-HER3 antibody if HRG gene expression at an mRNA level is assessed as low.

In some embodiments, the subject can be treated by electing to withhold or abstain from a treatment comprising an anti-HER3 antibody if HRG gene expression at an mRNA level is assessed as low or electing to administer a treatment comprising an anti-HER3 antibody if HRG gene expression at an mRNA level is assessed as high.

The anti-HER3 antibody can be any protein or ligand that can bind to HER3, such as those discussed above. In some embodiments, the anti-HER3 antibody is one or more of patritumab (U3-1287), duligotumab (MEHD-7945H), MM-111, LJM716, RG-7116, tri-specific anti-EGFR/ERBB3 zybody, huHER3-8 and seribantumab (MM-121).

The anti-HER3 antibody can be administered at any suitable dose. For example, the antibody can be administered at about 9 mg/kg or more, about 12 mg/kg or more, about 15 mg/kg or more, or about 18 mg/kg or more. In some embodiments, the antibody can be administered at about 9 mg/kg or less, about 12 mg/kg or less, about 15 mg/kg or less, or about 18 mg/kg or less.

The anti-HER3 antibody can be administered by any suitable method. For example, in some embodiments the antibody is administered intravenously. However, the administration route is not limited to the intravenous one, but can be any other suitable one as well.

In some embodiments, the anti-HER3 antibody is administered one or more times every week or more frequently, or, every two weeks, or every three weeks, or less frequently.

In some embodiments, the treatment comprises administering an anti-HER3 antibody in combination with a tyrosine kinase inhibitor or HER inhibitor, such as an epidermal growth factor receptor inhibitor. The treatment can comprise administering an anti-HER3 antibody in combination with, for example, one or more of trastuzumab, T-DM1, lapatinib, pertuzumab, cetuximab, panitumumab gefitinib, afatinib, dacomitinib, KD-019 and erlotinib.

In some embodiments, the treatment comprises administering an anti-HER3 antibody in combination with a chemotherapy. The treatment can comprise administering an anti-HER3 antibody in combination with, for example, one or more of such as cisplatin, 5-fluoruracil, paclitaxel, capecitabine, and other chemotherapies.

In some embodiments, the treatment comprises administering an anti-HER3 antibody in combination with both a tyrosine kinase inhibitor or HER inhibitor and chemotherapy. The treatment can comprise administering an anti-HER3 antibody in combination with, for example, one or more of trastuzumab, T-DM1, lapatinib, pertuzumab, cetuximab, panitumumab, gefitinib, dacomitinib, KD-019, afatinib, dacomitinib, KD-019 and erlotinib, and one or more of cisplatin, carboplatin, gemcitabine, permetrexed, irinotecan, 5-fluoruracil, paclitaxel, docetaxel, capecitabine, and other chemotherapies.

In some embodiments, the treatment comprises administering an anti-HER3 antibody in combination with radiotherapy. In some embodiments, treatment comprises administering an anti-HER3 antibody in combination with radiotherapy and one or more of a tyrosine kinase inhibitor, HER inhibitor, and chemotherapy.

In some embodiments, anti-HER3 antibodies can be administered in combination with first-line treatments for metastatic or locally advanced head and neck cancer, such as radiotherapy or radiation therapy, cetuximab, cisplatin, and/or 5-fluoruracil.

In some embodiments, anti-HER3 antibodies can be administered in combination with first-line treatments for NSCLC, such as erlotinib or platinum-based chemotherapy.

In some embodiments, anti-HER3 antibodies can be administered in combination with second-line treatments for NSCLC, such as docetaxel.

In some embodiments, anti-HER3 antibodies can be administered in combination with treatments for RAS wild-type cancer colorectal cancer and other cancer, such as cetuximab, panitumumab, and/or chemotherapy.

In some embodiments, anti-HER3 antibodies can be administered in combination with radiation, cisplatin, cetuximab, 5-fluoruracil, and/or other HER inhibitors or chemotherapies.

In some embodiments, anti-HER3 antibodies can be administered in combination with one or more of trastuzumab, paclitaxel, lapatinib, capecitabine, and/or other HER inhibitors or chemotherapies.

Test Kits

Also disclosed is a diagnostic test kit comprising certain components for performing methods of the invention. A diagnostic test kit enhances convenience, speed and reproducibility in the performance of diagnostic assays. For example, in an exemplary qRT-PCR-based embodiment, a basic diagnostic test kit includes PCR primers for analyzing expression of HRG. In other embodiments, a more elaborate test kit contains not only PCR primers, but also buffers, reagents and detailed instructions for measuring HRG expression levels, using PCR technology. In some embodiments, the kit includes a test protocol and all the consumable components needed for the test, except the RNA sample(s).

In an exemplary DNA microarray-based embodiment, a test kit includes a micro fluidic card (array) designed for use with a particular instrument. Optionally, the micro fluidic card is a custom made device designed specifically for measurement of HRG. Such custom micro fluidic cards are commercially available. For example, the TaqMan Array is a 384-well micro fluidic card (array) designed for use with the Applied Biosystems 7900HT Fast Real Time PCR System (Applied Biosystems, Foster City, CA).

In some embodiments, one or more TaqMan probes (Life Technologies Corporation; code Hs01101537_m1) can be used to amplify and detect the nucleotide sequence consisting of 72 nucleotides in GenBank Accession No. NM_013964.3. The center/middle of the amplified nucleotide sequence is located at the $1318^{th}$ nucleotide of the NM_013964.3. The amplified sequence is commonly found on mRNA of HRG-α, HRG-β1, HRG-β1b, HRG-β1c, HRG-β1d, HRG-β2, HRG-β2b, ndf43, ndf43b, and ndf43c.

The nucleotide sequence consisting of the nucleotides No. 1221 to 1780 of the NM_013964.3 is commonly found on the mRNA of many HRG variants. Therefore, the primers and/or probe for detecting HRG can be designed to amplify full-length or any partial sequence of the nucleotides No. 1221 to 1780 of the NM_013964.3.

Probes of PCR or microarray can be designed on the 3' end of mRNA or can be designed on a sequence of interest to detect particular form of transcript variant.

EXAMPLES

The invention is further illustrated by the following examples. The examples are provided for illustrative purposes only, and are not to be construed as limiting the scope or content of the invention in any way.

Abbreviations: AE—adverse event; CI—confidence interval: CR—complete response; DLT—dose limiting toxicity; FAS—full analysis set; FFPE—formalin-fixed, paraffin-embedded; HR—hazard ratio; IN—intravenous; ITT—intent to treat; MTD—maximum tolerated dose; NE—not evaluated; OS—overall survival; PD—progressive disease; PFS—progression-free survival; PH—proportional hazards; PO—oral; PR—partial response; SD—stable disease.

Example 1—Phase 1b/2 Clinical Trial

This and other examples provide the results of a randomized, placebo-controlled, double-blind Phase 1b/2 study designed to evaluate the safety and efficacy of patritumab in combination with erlotinib in EGFR-inhibitor treatment-naïve subjects with Stage IIIb/IV NSCLC who had progressed after at least 1 prior chemotherapy regimen. Unblinded data from the study is presented in Appendix A.

The study comprised a Phase 1b open-label, single-arm portion to assess safety and tolerability of patritumab in combination with erlotinib, and to determine the dosage for the Phase 2 portion, followed by a randomized, placebo-controlled Phase 2 portion to assess efficacy and safety of the combination therapy relative to erlotinib plus placebo. Based on Phase 1 study results in which a maximum tolerated dose was not reached, the preliminary human pharmacokinetic profile supported intravenous patritumab administration at or above 9 mg/kg once every 3 weeks to achieve circulating levels exceeding those showing maximal efficacy and pharmacodynamics in experimental animal models. A higher maintenance dose level of 18 mg/kg was also included to accommodate the possible effect of reduced tumor tissue penetration in the clinical setting relative to animal models. Due to the lack of dose limiting toxicity in a monotherapy Phase 1 study, the Phase 1b was designed as a dose-de-escalation study, with once daily oral administration of 150 mg of erlotinib and IV administration of 18 mg/kg patritumab every three weeks, with a provision for dose de-escalation from this maximal dose if it exceeded the MTD. As no DLTs were seen in this Phase 1b cohort, doses at this level and below were allowed in the Phase 2 portion.

In both portions of the study, subjects received 150 mg of erlotinib orally once daily. At the beginning of every 3 weeks treatment cycle, subjects received an IV infusion of patritumab or placebo (in Phase 2 portion). Three treatment regimens were evaluated: the combination of 150 mg erlotinib daily and 18 mg/kg patritumab every 3 weeks ("high dose"); the combination of 150 mg erlotinib daily and 18 mg/kg patritumab loading with 9 mg/kg patritumab maintenance every 3 weeks ("low dose"); and the combination of 150 mg erlotinib daily and placebo every 3 weeks ("placebo"). Tumors were to be assessed every 6 weeks (±3 days) up to the first 24 weeks of the study, then every 12 weeks (±7 days) independent of treatment cycle.

Based on blinded samples with respect to treatment group and clinical outcomes, an "HRG high" subject was defined as a subject with a delta Ct value of less than 3.9, the median value of the sample set. The delta Ct value was calculated using a mean of Ct values for three reference genes, and expression levels of HRG were determined based on the difference between the mean Ct value for HRG and the mean Ct value for the reference genes. All samples were assayed in triplicate.

HRG mRNA expression was measured by a qRT-PCR validated assay developed by MolecularMD. Total mRNA was first extracted from FFPE using Qiagen RNeasy FFPE, and cDNA was then obtained using a RT-PCR reaction. The cDNA was used in four PCR reactions including HRG and three reference genes (HMBS, EIF2BI, and IPO8). The average PCR efficiency and linearity was within 90 to 110% and ≥0.99, respectively. Intra-assay and inter-assay precision was conducted among 6 different FFPE samples starting from mRNA extraction from FFPE samples.

During assessment of intra-assay precision, RNA was extracted from FFPE samples once and six replicates were run in one run starting from RT-PCR reaction. During the PCR reaction, duplicate wells were run for each cDNA. The standard deviation of delta Ct in the intra-assay precision ranged from 0.11 to 0.89. The sample which had an standard deviation delta Ct of 0.89 appeared to include an outlier among its six data points.

During assessment of inter-assay precision, five separate RNA extractions were conducted for each sample for a total of six FFPE samples (a total of 30 RNA extractions). 30 RNA samples were run in five different batches. Each RNA proceeded to an RT-PCR reaction followed by a PCR reaction. Duplicate wells were run in a PCR reaction for each RNA sample. The standard deviation of delta Ct ranged from 0.06 to 0.58.

In the study, 188 tissue samples were collected from 215 randomized subjects; from these samples, reportable HRG qRT-PCR data were obtained for 102 subjects. The remaining 86 subjects had non-reportable HRG qRT-PCR results: 42 samples lacked sufficient tumor/tissue material, 38 lacked sufficient RNA, and 6 samples yielded non-reportable Ct values.

The sample size for the Phase 2 portion was calculated based on a one-sided log-rank test with 80% power to detect a 50% improvement (that is, HR of 0.667) in median PFS of 3.3 vs 2.2 months between any patritumab arm compared to the control at a significance level of one-sided alpha=0.1.

The primary analyses for this study occurred when 162 PFS events (and 110 PFS events per comparison of patritumab 18 mg/kg+erlotinib and control arms, and of patritumab 9 mg/kg+erlotinib and control arms) had been observed. At the point of primary analysis, the treatment assignment for all subjects was unblinded to designated study personnel for analysis after data were reconciled and cleaned, and a snapshot of the clean database was created. To minimize potential bias, individual treatment assignment was not divulged to subjects or Investigators until study closure.

All efficacy analyses were performed on the full analysis set, which includes all subjects in the randomized analysis set who received at least one dose of randomized study medication. The primary efficacy endpoint was PFS. PFS is defined as the time from the date of randomization to the earlier of the dates of the first objective documentation of radiographic disease progression or death due to any cause. A subject who was alive with no objective documentation of (radiographic) disease progression by the data cut-off date was to be censored at the date of the last evaluable tumor assessment. The key secondary efficacy endpoint, overall survival, was defined as the time from the date of randomization to death due to any cause and was analyzed in the same manner as the primary efficacy endpoint PFS.

The primary analysis for PFS used a stratified log-rank linear trend test for the dose-response relationship, followed by pair-wise comparisons of each patritumab arm and the control using the stratified log-rank test, accounting for the stratification factors at randomization: histology (Adenocarcinoma vs Non-Adenocarcinoma) and best response to prior therapy (CR/PR vs SD vs PD). Kaplan-Meier curves were generated for PFS and used to calculate medians and 95% CIs for each treatment group. Estimates of the HR between each patritumab arm and the control along with 95% CIs were calculated using a stratified Cox's proportional hazards model.

The primary analysis for PFS in HRG-high group on the FAS used a stratified log-rank test for the comparisons of each patritumab arm and the control and the comparison of the combined patritumab arm and the control. The stratification factors included histology (Adenocarcinoma vs Non-Adenocarcinoma) and best response to prior therapy (CR/PR/SD vs PD). Estimates of the HR between each patritumab arm and the control and between the combined patritumab arm and the control along with 95% CIs were calculated using a stratified Cox's proportional hazards model with the same stratification factors used for the stratified log-rank test.

Unless otherwise indicated, log-rank p-values and HRs for PFS and OS were based on the primary analysis adjusted for the stratification factors at randomization as described above.

The Phase 1b portion of the trial enrolled 7 subjects (4 male; median age [range], 68 years [48-78]) all of whom received the combination of 150 mg erlotinib daily and 18 mg/kg patritumab every 3 weeks. AEs grade ≥3 occurred in 2 subjects: one grade 3 case each of pain, fatigue, headache, dehydration, diarrhea, and blood creatinine increase; none were related to patritumab. Three subjects had four serious AEs: grade 3 pain (unrelated to study treatment), grade 3 dehydration (erlotinib-related), and grade 1 decreased appetite (erlotinib- and patritumab-related) and grade 1 pyrexia (unrelated) in one subject. Most reported AEs were grade 1 or 2 and were considered erlotinib-related. The only patritumab-related AE reported in ≥2 subjects was decreased appetite (2 subjects).

No response was recorded and stable disease was noted in four subjects (83, 87, 90, and 117 days). All 7 subjects discontinued from study treatment due to disease progression; 6 subjects were followed until death, and 1 subject withdrew consent for follow-up.

No DLTs were reported during the phase 1b study. Therefore, the Phase 2 dose regimens were a patritumab 18 mg/kg loading dose, with subsequent administration of either a 9 mg/kg patritumab or 18 mg/kg patritumab maintenance dose every 3 weeks. Subjects were also administered 150 mg/day erlotinib during the phase 2 trial.

For the Phase 2 portion, 3 subjects were randomized but not treated, thus there were 212 subjects in the FAS and safety analysis set. The analysis results presented below are based on primary analyses of efficacy data (except for OS) from the locked database (as of data cut-off date Oct. 30, 2012). OS data was not mature yet at the time of primary analysis, and the preliminary results from updated OS analysis based on a data cut-off date of Apr. 19, 2013 are presented below.

Dispositions of the 215 subjects enrolled into the randomized Phase 2 portion of the study are summarized in Table 1. Demographic information for the full analysis set is summarized in Table 2. There was no meaningful difference among treatment groups with respect to demographic characteristics.

TABLE 1

Phase 2 Subject Disposition

| | Subject Accounting | Placebo + erlotinib (N = 71) | 18 mg/kg + erlotinib (N = 72) | 9 mg/kg + erlotinib (N = 72) | Total Phase 2 (N = 215) |
|---|---|---|---|---|---|
| Treatment Status | Enrolled/Randomized but Not Dosed | 0 | 2 (2.8%) | 1 (1.4%) | 3 (1.4%) |
| | Ongoing on the Study Treatment | 5 (7.0%) | 5 (6.9%) | 6 (8.3%) | 16 (7.4%) |
| | Discontinued from Study Treatment | 66 (93.0%) | 65 (90.3%) | 65 (90.3%) | 196 (91.2%) |
| Primary Reason for Discontinuing Study Treatment | Adverse Event | 5 (7.0%) | 7 (9.7%) | 6 (8.3%) | 18 (8.4%) |
| | Lost to Follow-up | 0 | 0 | 0 | 0 |
| | Death | 4 (5.6%) | 11 (15.3%) | 2 (2.8%) | 17 (7.9%) |
| | Protocol Violation | 0 | 0 | 0 | 0 |
| | Subject Withdrew Consent | 3 (4.2%) | 2 (2.8%) | 4 (5.6%) | 9 (4.2%) |
| | Study Terminated by Sponsor | 0 | 0 | 0 | 0 |
| | Progressive Disease (Radiographic Progression) | 50 (70.4%) | 42 (58.3%) | 45 (62.5%) | 137 (63.7%) |
| | Other | 4 (5.6%) | 3 (4.2%) | 8 (11.1%) | 15 (7.0%) |
| On-Study Death[a] | | 13 (18.3%) | 20 (27.8%) | 9 (12.5%) | 42 (19.5%) |
| Primary Cause of On-Study Death | Adverse Event | 5 (7.0%) | 11 (15.3%) | 4 (5.6%) | 20 (9.3%) |
| | Disease Progression | 8 (11.3%) | 8 (11.1%) | 4 (5.6%) | 20 (9.3%) |
| | Unknown | 0 | 0 | 1 (1.4%) | 1 (0.5%) |
| | Other | 0 | 1 (1.4%) | 0 | 1 (0.5%) |

Notes:
Percentages are based on the number of subjects in the Enrolled/Randomized Analysis Set.
[a]On-Study Death = Y if the date of death occurred on or after the date of first drug administration and within the AE collection period (up to 53 days after the last dose of patritumab or more than 30 days after the last dose of erlotinib, whichever is later).

TABLE 2

Demographic and Baseline Characteristics (Full Analysis Set)

| | Placebo + erlotinib (N = 71) | 18 mg/kg erlotinib (N = 70) | 9 mg/kg + erlotinib (N = 71) | Total (N = 212) |
|---|---|---|---|---|
| Age (yrs) [a] | | | | |
| Median | 60.0 | 62.0 | 65.0 | 62.5 |
| Minimum | 35 | 41 | 44 | 35 |
| Maximum | 88 | 82 | 84 | 88 |
| <60 | 33 (46.5%) | 28 (40.0%) | 24 (33.8%) | 85 (40.1%) |
| >=60 | 38 (53.5%) | 42 (60.0%) | 47 (66.2%) | 127 (59.9%) |
| Gender | | | | |
| Male | 43 (60.6%) | 38 (54.3%) | 48 (67.6%) | 129 (60.8%) |
| Female | 28 (39.4%) | 32 (45.7%) | 23 (32.4%) | 83 (39.2%) |
| Race | | | | |
| White | 69 (97.2%) | 68 (97.1%) | 71 (100.0%) | 208 (98.1%) |
| Black or African American | 1 (1.4%) | 1 (1.4%) | 0 | 2 (0.9%) |
| Asian | 0 | 1 (1.4%) | 0 | 1 (0.5%) |
| Other/Specify | 1 (1.4%) | 0 | 0 | 1 (0.5%) |
| Weight (kg) | | | | |
| n | 71 | 70 | 71 | 212 |
| Mean | 74.68 | 73.59 | 72.34 | 73.53 |
| SD | 14.337 | 17.506 | 14.369 | 15.422 |
| Median | 74.00 | 72.00 | 7230 | 72.55 |
| Minimum | 42.6 | 44.0 | 42.0 | 42.0 |
| Maximum | 108.6 | 121.0 | 114.0 | 121.0 |
| Smoking Status | | | | |
| Never | 5 (7.0%) | 10 (14.3%) | 11 (15.5%) | 26 (12.3%) |
| Current | 13 (18.3%) | 12 (17.1%) | 9 (12.7%) | 34 (16.0%) |
| Former | 53 (74.6%) | 48 (68.6%) | 51 (71.8%) | 152 (71.7%) |
| Pack Years (PY) | | | | |
| <=15 PY | 11 (15.5%) | 9 (12.9%) | 7 (9.9%) | 27 (12.7%) |
| >15 PY | 50 (70.4%) | 43 (61.4%) | 47 (66.2%) | 140 (66.0%) |
| Missing | 10 (14.1%) | 18 (25.7%) | 17 (23.9%) | 45 (21.2%) |

Notes:
Denominator for percentages is the number of subjects in the FAS.
[a]: Age in years is calculated using the informed consent date and the birth date Subject baseline characteristics with regard to NSCLC history and prior therapy are shown in Table 3. Subjects generally appeared to be well balanced among treatment groups.

TABLE 3

Baseline Prognostic and Disease Characteristics (Full Analysis Set)

| | Placebo + erlotinib (N = 71) | 18 mg/kg + erlotinib (N = 70) | 9 mg/kg + erlotinib (N = 71) | Total (N = 212) |
|---|---|---|---|---|
| Baseline ECOG Performance Status | | | | |
| 0 Fully Active | 25 (35.2%) | 33 (47.1%) | 30 (42.3%) | 88 (41.5%) |
| 1 Restricted in Physically Strenuous Activity | 46 (64.8%) | 37 (52.9%) | 41 (57.7%) | 124 (58.5%) |
| Histology | | | | |
| Adenocarcinoma | 42 (59.2%) | 46 (65.7%) | 44 (62.0%) | 132 (62.3%) |
| Squamous | 21 (29.6%) | 19 (27.1%) | 23 (32.4%) | 63 (29.7%) |
| Other | 8 (11.3%) | 5 (7.1%) | 4 (5.6%) | 17 (8.0%) |
| NSCLC Tumor Staging at Study Entry (CRF) | | | | |
| IIIB | 7 (9.9%) | 5 (7.1%) | 9 (12.7%) | 21 (9.9%) |
| IV | 64 (90.1%) | 65 (92.9%) | 62 (87.3%) | 191 (90.1%) |
| Time from initial Diagnosis of NSCLC to Study Treatment (months) | | | | |
| <6 months | 10 (14.1%) | 16 (22.9%) | 14 (19.7%) | 40 (18.9%) |
| 6-12 months | 37 (52.1%) | 33 (47.1%) | 35 (49.3%) | 105 (49.5%) |
| >12 months | 24 (33.8%) | 21 (30.0%) | 22 (31.0%) | 67 (31.6%) |
| Number of Prior NSCLC Therapies | | | | |
| 0 | 0 | 0 | 0 | 0 |
| 1 | 47 (66.2%) | 50 (71.4%) | 48 (67.6%) | 145 (68.4%) |
| 2 | 24 (33.8%) | 19 (27.1%) | 22 (31.0%) | 65 (30.7%) |
| 3 | 0 | 1 (1.4%) | 1 (1.4%) | 2 (0.9%) |
| Best Response to Prior Chemotherapy[a] | | | | |
| CR/PR | 23 (32.4%) | 19 (27.1%) | 17 (23.9%) | 59 (27.8%) |
| SD | 29 (40.8%) | 28 (40.0%) | 34 (47.9%) | 91 (42.9%) |
| PD | 19 (26.8%) | 23 (32.9%) | 20 (28.2%) | 62 (29.2%) |
| Exposure to Prior Platinum Therapy | | | | |
| Yes | 70 (98.6%) | 70 (100.0%) | 70 (98.6%) | 210 (99.1%) |
| No | 1 (1.4%) | 0 | 1 (1.4%) | 2 (0.9%) |
| Prior Radiation Therapy | | | | |
| Yes | 24 (33.8%) | 25 (35.7%) | 22 (31.0%) | 71 (33.5%) |
| No | 47 (66.2%) | 45 (64.3%) | 49 (69.0%) | 141 (66.5%) |

Notes:
Percentages reflect proportion of subjects in Full Analysis Set (FAS).
Baseline = last non-missing value before initial administration of study treatment.
[a]If a subject has two lines of prior chemotherapy regimens, the best response to the most recent chemotherapy regimen (excluding 'Not Applicable') was used.

Possible predictive/prognostic biomarker data for the FAS are shown in Table 4. Treatment groups appeared to be balanced with respect to expression levels of HER3 and HRG and EGFR mutation status.

TABLE 4

Baseline Possible Predictive/Prognostic Biomarkers (Full Analysis Set)

| | Placebo + erlotinib (N = 71) | 18 mg/kg + erlotinib (N = 70) | 9 mg/kg + erlotinib (N = 71) | Total (N = 212) |
|---|---|---|---|---|
| Possible Predictive/Prognostic Biomarkers | | | | |
| HER3[a] | | | | |
| Positive | 21 (29.6%) | 31 (44.3%) | 24 (33.8%) | 76 (35.8%) |
| Extreme Overexpression | 0 | 3 (4.3%) | 1 (1.4%) | 4 (1.9%) |
| Negative | 30 (42.3%) | 21 (30.0%) | 25 (35.2%) | 76 (35.8%) |
| Unknown | 20 (28.2%) | 18 (25.7%) | 22 (31.0%) | 60 (28.3%) |

TABLE 4-continued

Baseline Possible Predictive/Prognostic Biomarkers (Full Analysis Set)

|  | Placebo + erlotinib (N = 71) | 18 mg/kg + erlotinib (N = 70) | 9 mg/kg + erlotinib (N = 71) | Total (N = 212) |
|---|---|---|---|---|
| HRG[b] | | | | |
| High | 19 (26.8%) | 17 (24.3%) | 16 (22.5%) | 52 (24.5%) |
| Low | 16 (22.5%) | 19 (27.1%) | 15 (21.1%) | 50 (23.6%) |
| Unknown | 36 (50.7%) | 34 (48.6%) | 40 (56.3%) | 110 (51.9%) |
| EGFR Mutation Status from tissue or plasma | | | | |
| Sensitizing Only | 2 (2.8%) | 0 | 3 (4.2%) | 5 (2.4%) |
| Resistance Only | 0 | 1 (1.4%) | 0 | 1 (0.5%) |
| Both Sensitizing and Resistance | 0 | 0 | 0 | 0 |
| Wild Type | 47 (66.2%) | 45 (64.3%) | 47 (66.2%) | 139 (65.6%) |
| Unknown | 22 (31.0%) | 24 (34.3%) | 21 (29.6%) | 67 (31.6%) |
| EGFR Mutation Status from tissue | | | | |
| Sensitizing Only | 2 (2.8%) | 0 | 2 (2.8%) | 4 (1.9%) |
| Wild Type | 23 (32.4%) | 17 (24.3%) | 21 (29.6%) | 61 (28.8%) |
| Unknown | 46 (64.8%) | 53 (75.7%) | 48 (67.6%) | 147 (69.3%) |

Notes:
Denominator for percentages is the number of subjects in the Full Analysis Set (FAS).
The baseline value is defined as the last non-missing value before initial administration of study treatment.
[a]HER3 positive is defined as membrane staining H-score > 0;
HER3 negative is defined as a membrane staining H-score = 0;
HER3 extreme overexpression is defined as a membrane staining H-score > 100.
[b]HER3 high is defined as delta Ct value < 3.9;
HRG low is defined as delta Ct value ≥ 3.9.

Demographic information for subjects with tumors expressing high HRG levels are summarized in Table 5. There was no meaningful difference among treatment groups with respect to demographic characteristics; however, 3 of 16 subjects were never-smokers in the low dose group, one of the 17 subjects was a never-smoker in the high dose group and none of 19 subjects was a never-smoker in the placebo group. An analysis performed eliminating the never smokers did not change the results stated below.

TABLE 5

Demographic and Baseline Characteristics in Subjects with Tumors Expressing High Heregulin (HRG) Levels

|  | Placebo + erlotinib (N = 18) | 18 mg/kg + erlotinib (N = 17) | 9 mg/kg + erlotinib (N = 16) | Total (N = 51) |
|---|---|---|---|---|
| Age (yrs)[a] | | | | |
| Median | 60.0 | 63.0 | 66.0 | 64.0 |
| Minimum | 46 | 50 | 57 | 46 |
| Maximum | 76 | 74 | 77 | 77 |
| <60 | 9 (50.0%) | 6 (35.3%) | 3 (18.8%) | 18 (35.3%) |
| ≥60 | 9 (50.0%) | 11 (64.7%) | 13 (81.3%) | 33 (64.7%) |
| Gender | | | | |
| Male | 12 (66.7%) | 11 (64.7%) | 9 (56.3%) | 32 (62.7%) |
| Female | 6 (33.3%) | 6 (35.3%) | 7 (43.8%) | 19 (37.3%) |
| Race | | | | |
| White | 18 (100.0%) | 17 (100.0%) | 16 (100.0%) | 51 (100.0%) |
| Weight (kg) | | | | |
| Mean | 73.39 | 64.97 | 71.29 | 69.93 |
| SD | 12.891 | 15.407 | 14.053 | 14.317 |
| Median | 72.50 | 63.00 | 72.50 | 69.70 |
| Minimum | 48.2 | 44.0 | 42.0 | 42.0 |
| Maximum | 90.0 | 99.0 | 90.0 | 99.0 |
| Smoking Status | | | | |
| Never | 0 | 1 (5.9%) | 3 (18.8%) | 4 (7.8%) |
| Current | 5 (27.8%) | 4 (23.5%) | 2 (12.5%) | 11 (21.6%) |
| Former | 13 (72.2%) | 12 (70.6%) | 11 (68.8%) | 36 (70.6%) |

TABLE 5-continued

Demographic and Baseline Characteristics in Subjects with Tumors Expressing High Heregulin (HRG) Levels

|  | Placebo + erlotinib (N = 18) | 18 mg/kg + erlotinib (N = 17) | 9 mg/kg + erlotinib (N = 16) | Total (N = 51) |
|---|---|---|---|---|
| Pack Years (PY) |  |  |  |  |
| ≤15 PY | 3 (16.7%) | 4 (23.5%) | 0 | 7 (13.7%) |
| >15 PY | 14 (77.8%) | 11 (64.7%) | 11 (68.8%) | 36 (70.6%) |
| Missing | 1 (5.6%) | 2 (11.8%) | 5 (31.3%) | 8 (15.7%) |

Notes:
Denominator for percentages is the number of subjects with high HRG expression tumors in the Full Analysis Set.
High HRG expression is defined as delta Ct value < 3.9.
[a]Age in years is calculated using the informed consent date and the birth date.

Subject baseline characteristics with regard to NSCLC history and prior therapy are shown in Table 6. Subjects generally appeared to be well balanced among treatment groups with respect to baseline characteristics; however, there were 3 (18.8%) subjects in the low dose group, no subject in the high dose group and 6 (31.6%) subjects in the placebo group with best response to most recent prior therapy being CR/PR. For subjects with 2 prior therapies, there were 8 (50%) subjects in the low dose group, 4 (23.5%) subjects in the high dose and 5 (26.3%) subjects in the placebo group.

TABLE 6

Baseline Prognostic and Disease Characteristics in Subjects with Tumors Expressing High Heregulin (HRG) Levels

|  | Placebo + erlotinib (N = 18) | 18 mg/kg + erlotinib (N = 17) | 9 mg/kg + erlotinib (N = 16) | Total (N = 51) |
|---|---|---|---|---|
| Baseline ECOG Performance Status |  |  |  |  |
| 0-Fully Active | 9 (50.0%) | 9 (52.9%) | 7 (43.8%) | 25 (49.0%) |
| 1-Restricted in Physically Strenuous Activity | 9 (50.0%) | 8 (47.1%) | 9 (56.3%) | 26 (51.0%) |
| Histology |  |  |  |  |
| Adenocarcinoma | 8 (44.4%) | 8 (47.1%) | 8 (50.0%) | 24 (47.1%) |
| Squamous | 10 (55.6%) | 8 (47.1%) | 7 (43.8%) | 25 (49.0%) |
| Other | 0 | 1 (5.9%) | 1 (6.3%) | 2 (3.9%) |
| NSCLC Tumor Staging at Study Entry (CRF) |  |  |  |  |
| IIIB | 0 | 2 (11.8%) | 3 (18.8%) | 5 (9.8%) |
| IV | 18 (100%) | 15 (88.2%) | 13 (81.3%) | 46 (90.2%) |
| Time from Initial Diagnosis of NSCLC to Study Treatment (months) |  |  |  |  |
| <6 months | 0 | 3 (17.6%) | 3 (18.8%) | 6 (11.8%) |
| 6-12 months | 12 (66.7%) | 7 (41.2%) | 7 (43.8%) | 26 (51.0%) |
| >12 months | 6 (33.3%) | 7 (41.2%) | 6 (37.5%) | 19 (37.3%) |
| Number of Prior NSCLC Therapies |  |  |  |  |
| 0 | 0 | 0 | 0 | 0 |
| 1 | 13 (72.2%) | 13 (76.5%) | 8 (50.0%) | 34 (66.7%) |
| 2 | 5 (27.8%) | 4 (23.5%) | 8 (50.0%) | 17 (33.3%) |
| Best Response to Prior Chemotherapy[a] |  |  |  |  |
| CR/PR | 5 (27.8%) | 0 | 3 (18.8%) | 8 (15.7%) |
| SD | 8 (44.4%) | 11 (64.7%) | 8 (50.0%) | 27 (52.9%) |
| PD | 5 (27.8%) | 6 (35.3%) | 5 (31.3%) | 16 (31.4%) |
| Exposure to Prior Platinum Therapy |  |  |  |  |
| Yes | 18 (100.0%) | 17 (100.0%) | 16 (100.0%) | 51 (100.0%) |
| No | 0 | 0 | 0 | 0 |

TABLE 6-continued

Baseline Prognostic and Disease Characteristics in Subjects with Tumors
Expressing High Heregulin (HRG) Levels

| | Placebo + erlotinib (N = 18) | 18 mg/kg + erlotinib (N = 17) | 9 mg/kg + erlotinib (N = 16) | Total (N = 51) |
|---|---|---|---|---|
| Prior Radiation Therapy | | | | |
| Yes | 4 (22.2%) | 7 (41.2%) | 4 (25.0%) | 15 (29.4%) |
| No | 14 (77.8%) | 10 (58.8%) | 12 (75.0%) | 36 (70.6%) |

Notes:
Denominator for percentages is the number of subjects with high HRG-expressing tumors in the Full Analysis Set.
High HRG expression is defined as delta Ct value < 3.9.
[a]If a subject has two lines of prior chemotherapy regimens, the best response to the most recent chemotherapy regimen (excluding 'Not Applicable') will be used.

Possible predictive/prognostic biomarker values for subjects with tumors expressing high levels of HRG are summarized in Table 7. Treatment groups appeared to be balanced with respect to expression level of HER3. A single subject in the low dose group, a single subject in the placebo group and no subject in the high dose group had known EGFR mutations. A slightly larger proportion of subjects in the high-dose group had unknown EGFR mutational status as compared to the placebo group and the low dose group.

Figure 2:
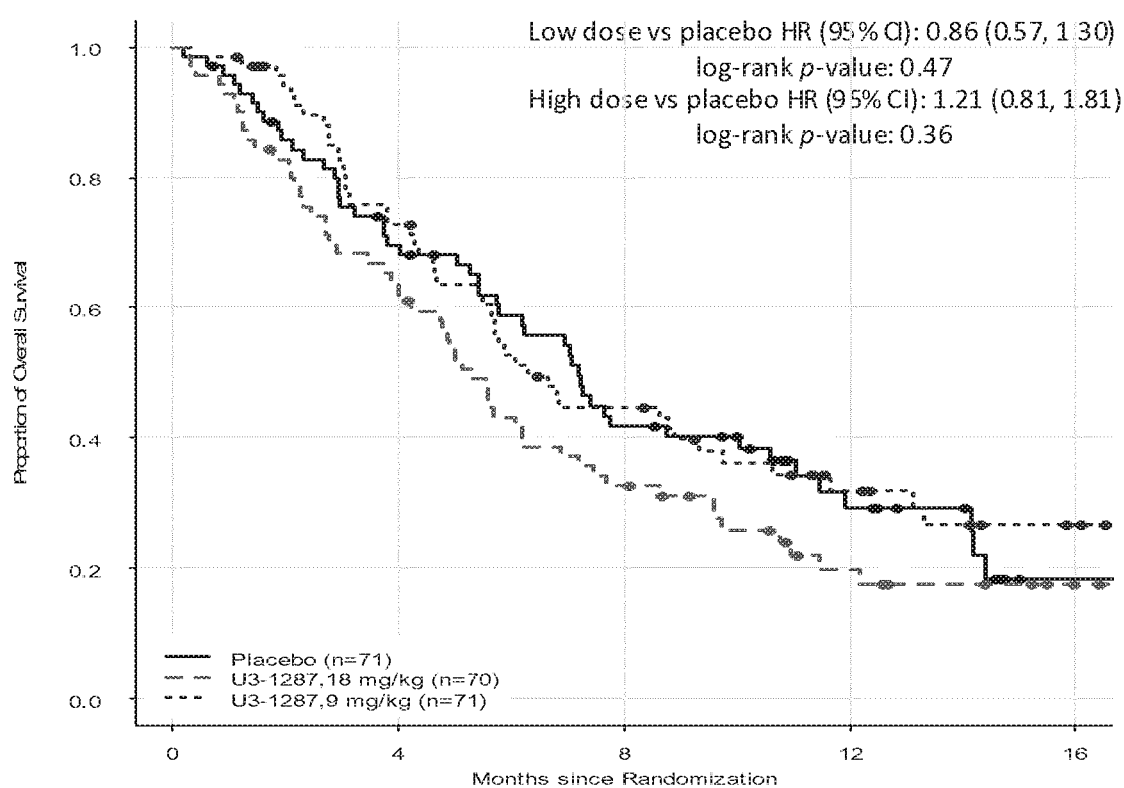
FIG. 2 depicts overall survival (showing high- and low-dose patritumab+erlotinib vs. placebo+erlitonib) for all subjects from the study in Example 2.

Example 2—Progression Free Survival and Overall Survival in Full Analysis Set The primary analysis of PFS for the FAS is presented in Table 8. Kaplan-Meier estimates of progression-free survival in the FAS are presented in FIG. 1 (showing high- and low-dose patritumab+erlotinib vs. placebo+erlitonib). Overall Survival (OS) results in the unselected FAS are presented in Table 9 and FIG. 2 (showing high- and low-dose patri-

TABLE 7

Baseline Possible Predictive/Prognostic Biomarkers in Subjects with Tumors
Expressing High Heregulin (HRG) Levels

| | Placebo + erlotinib (N = 18) | 18 mg/kg + erlotinib (N = 17) | 9 mg/kg + erlotinib (N = 16) | Total (N = 51) |
|---|---|---|---|---|
| HER3[a] | | | | |
| High Expression | 10 (55.6%) | 10 (58.8%) | 8 (50.0%) | 28 (54.9%) |
| Extreme Overexpression | 0 | 2 (11.8%) | 0 | 2 (3.9%) |
| Low Expression | 8 (44.4%) | 5 (29.4%) | 8 (50.0%) | 21 (41.2%) |
| Unknown | 0 | 2 (11.8%) | 0 | 2 (3.9%) |
| EGFR Mutation Status from tissue or plasma | | | | |
| Sensitizing Only | 1 (5.6%) | 0 | 1 (6.2%) | 2 (3.9%) |
| Resistance Only | 0 | 1 (5.9%) | 0 | 1 (2.0%) |
| Both Sensitizing and Resistance | 0 | 0 | 0 | 0 |
| Wild Type | 14 (77.8%) | 9 (52.9%) | 11 (68.8%) | 34 (66.7%) |
| Unknown | 3 (16.7%) | 7 (41.2%) | 4 (25.0%) | 14 (27.5%) |
| EGFR Mutation Status from tissue | | | | |
| Sensitizing Only | 1 (5.5%) | 0 | 1 (6.2%) | 2 (3.9%) |
| Wild Type | 9 (50.0%) | 5 (29.4%) | 7 (43.8%) | 21 (41.2%) |
| Unknown | 8 (44.4%) | 12 (70.6%) | 8 (50.0%) | 28 (54.9%) |

Notes:
Denominator for percentages is the number of subjects with high HRG-expressing tumors in the Full Analysis Set.
High HRG expression is defined as delta Ct value < 3.9.
[a]HER3 high expression is defined as membrane staining H-score > 0;
HER3 low expression is defined as a membrane staining H-score = 0;
HER3 extreme overexpression is defined as a membrane staining H-score > 100.

tumab+erlotinib vs. placebo+erlitonib). There was no significant improvement in PFS or OS for the combination of patritumab with erlotinib as compared to erlotinib plus placebo in the full analysis set, and the study was considered as negative for the unselected ITT population.

The number of subjects with the response being CR/PR in low- and high-dose patritumab treatment groups were respectively 9 (12.9%) and 5 (7.1%) vs placebo 4 (5.6%).

TABLE 8

Analysis of Progression-Free Survival in Full Analysis Set

|  | Placebo + erlotinib (N = 71) | 18 mg/kg + erlotinib (N = 70) | 9 mg/kg + erlotinib (N = 71) |
|---|---|---|---|
| Subjects (%) with events | 59 (83.1%) | 58 (82.9%) | 52 (73.2%) |
| Subjects (%) without events (censored) | 12 (16.9%) | 12 (17.1%) | 19 (26.8%) |
| Time to event (months) [a] | | | |
| Median | 1.6 | 1.4 | 2.5 |
| 95% CI for Median | [1.4; 2.6] | [1.3; 2.7] | [1.5; 3.0] |
| Stratified Logrank P-Value [b] | | 0.9735 | 0.1512 |
| Hazard Ratio (relative to Placebo) [b] | | 0.978 | 0.770 |
| 95% CI | | [0.674; 1.420] | [0.523; 1.131] |
| 80% CI | | [0.767; 1.248] | [0.598; 0.990] |
| P-value for Hazard Ratio | | 0.9075 | 0.1828 |

Notes:
PFS is defined as the time from the randomization date to the date of the first objective documentation of disease progression or death resulting from any cause, whichever comes first.
[a] Kaplan-Meier Estimate.
CI for median was computed using the Brookmeyer-Crowley method.
[b] Stratified log-rank and stratified Cox PH were stratified by best response to prior therapy and histology subtype (Adenocarcinoma vs. Non-Adenocarcinoma).

TABLE 9

Analysis of Overall Survival in Full Analysis Set

|  | Placebo + erlotinib (N = 71) | 18 mg/kg + erlotinib (N = 70) | 9 mg/kg + erlotinib (N = 71) |
|---|---|---|---|
| Subjects (%) with events | 48 (67.6%) | 54 (77.1%) | 46 (64.8%) |
| Subjects (%) without events (censored) | 23 (32.4%) | 16 (22.9%) | 25 (35.2%) |
| Time to event (months) [a] | | | |
| Median | 7.2 | 5.3 | 6.3 |
| 95% CI for Median | [5.4; 10.6] | [4.0; 6.9] | [5.4; 9.3] |
| Stratified Logrank P-Value [b] | | 0.3823 | 0.3673 |
| Hazard Ratio (relative to Placebo) [b] | | 1.208 | 0.858 |
| 95% CI | | [0.807; 1.808] | [0.566; 1.301] |
| 80% CI | | [0.928; 1.572] | [0.653; 1.127] |
| P-value for Hazard Ratio | | 0.3585 | 0.4712 |

Notes:
OS is defined as the time from the randomization date to the date of death.
[a] Kaplan-Meier Estimate.
CI for median was computed using the Brookmeyer-Crowley method.
[b] Stratified log-rank and stratified Cox PH were stratified by best response to prior therapy and histology subtype (adenocarcinoma vs. non-adenocarcinoma).

Figure 3:
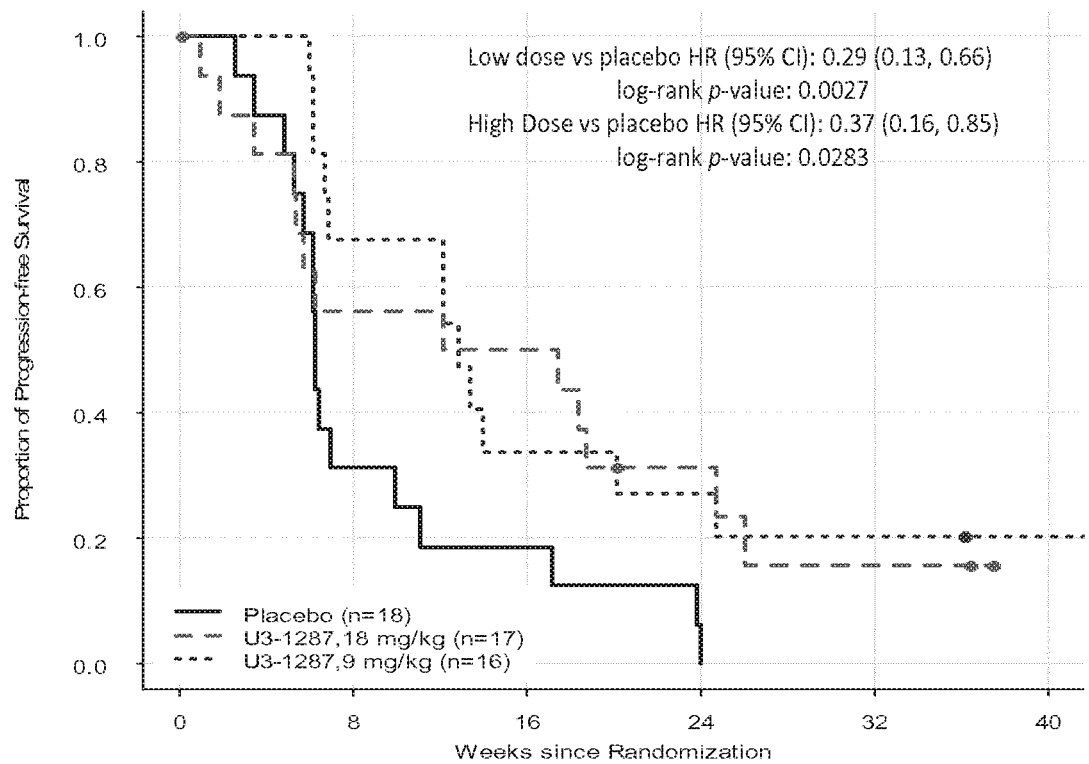
FIG. 3 depicts progression free survival (showing high- and low-dose patritumab+erlotinib vs. placebo+erlitonib) for subjects from the study in Example 3 assessed as having high HRG gene expression at an mRNA level.
Figure 4:
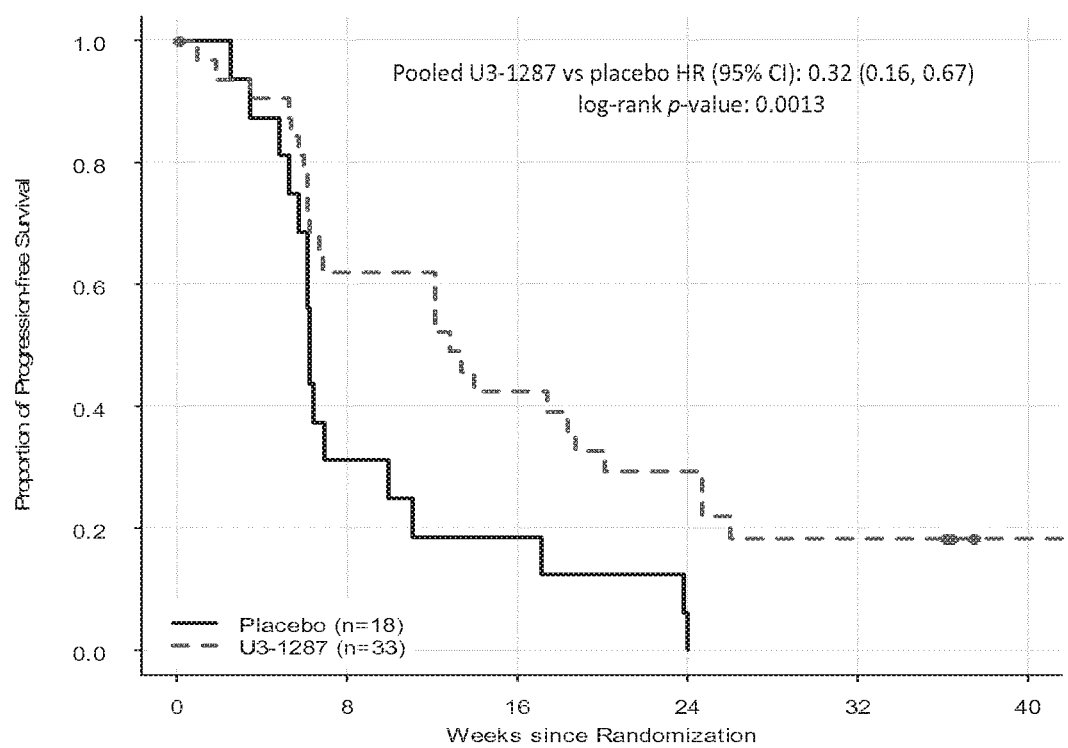
FIG. 4 depicts progression free survival (showing pooled patritumab+erlotinib vs. placebo+erlitonib) for subjects from the study in Example 3 assessed as having high HRG gene expression at an mRNA level.

Example 3—Progression Free Survival in Subjects with Tumors Expressing High HRG Levels Secondary analyses of PFS for the prospective subpopulation of subjects with tumors expressing high levels of HRG are presented in Table 10 and Table 11. Kaplan-Meier estimates of progression-free survival in subjects with tumors expressing high HRG at an mRNA level, defined as dCt<3.9, are presented in FIG. 3 (showing high- and low-dose patritumab+erlotinib vs. placebo+erlitonib) and FIG. 4 (showing pooled patritumab+erlotinib vs. placebo+erlotinib).

TABLE 10

Analysis of Progression-Free Survival in Subjects with Tumors Expressing High HRG Levels

|  | Placebo + erlotinib (N = 18) | 18 mg/kg + erlotinib (N = 17) | 9 mg/kg + erlotinib (N = 16) | Doses Combined (N = 33) |
|---|---|---|---|---|
| Subjects (%) with events | 16 (88.9%) | 13 (76.5%) | 12 (75.0%) | 25 (75.8%) |
| Subjects (%) without events censored | 2 (11.1%) | 4 (23.5%) | 4 (25.0%) | 8 (24.2%) |
| Time to event (months) [a] | | | | |
| Median | 1.4 | 3.4 | 3.0 | 3.0 |
| 95% CI for Median | [1.2; 2.3] | [1.2; 5.7] | [1.5; 5.7] | [1.4; 4.3] |
| PFS Rate at 8 Weeks (%) | 31.3% | 56.3% | 67.7% | 62.1% |
| 95% CI | [11.4; 53.6] | [29.5; 76.2] | [38.8; 85.2] | [42.9; 76.4] |
| PFS Rate at 14 Weeks (%) | 18.8% | 50.0% | 33.9% | 42.5% |
| 95% CI | [4.6; 40.2] | [24.5; 71.0] | [12.4; 57.0] | [25.1; 58.8] |
| PFS Rate at 26 Weeks (%) | 0.0% | 15.6% | 20.3% | 18.4% |
| 95% CI | [0.0; 0.0] | [2.8; 38.2] | [5.0; 42.9] | [7.0; 34.0] |
| Stratified Logrank P-Value [b] | | 0.0283 | 0.0027 | 0.0013 |

TABLE 10-continued

Analysis of Progression-Free Survival in Subjects with Tumors Expressing High HRG Levels

|  | Placebo + erlotinib (N = 18) | 18 mg/kg + erlotinib (N = 17) | 9 mg/kg + erlotinib (N = 16) | Doses Combined (N = 33) |
|---|---|---|---|---|
| Stratified Analysis [b] | | | | |
| Hazard Ratio (relative to Placebo) | | 0.369 | 0.288 | 0.324 |
| 95% CI | | [0.161; 0.846] | [0.125; 0.663] | [0.156; 0.672] |
| 80% CI | | [0.215; 0.635] | [0.167; 0.497] | [0.201; 0.522] |
| P-value for Hazard Ratio | | 0.0185 | 0.0034 | 0.0024 |

Notes:
PFS is defined as the time from the randomization date to the date of the first objective documentation of disease progression or death resulting from any cause, whichever comes first.
[a] Kaplan-Meier Estimate.
CI for median was computed using the Brookmeyer-Crowley method.
[b] Stratified log-rank and stratified Cox PH were stratified by best response to prior therapy (CR, PR, SD vs PD) and histology subtype (adenocarcinoma vs non-adenocarcinoma).

TABLE 11

Supportive Analyses of Progression-Free Survival in Subjects with Tumors Expressing High HRG Levels

|  | 18 mg/kg + erlotinib (N = 17) | 9 mg/kg + erlotinib (N = 16) | Doses Combined (N = 33) |
|---|---|---|---|
| Logrank P-value (unstratified) | 0.0583 | 0.0122 | 0.0089 |
| Stratified Logrank P-Value [a] | 0.0199 | 0.0009 | 0.0005 |
| Stratified Analysis[a] | | | |
| Hazard Ratio (relative to Placebo) | 0.332 | 0.252 | 0.287 |
| 95% CI | [0.141; 0.781] | [0.107; 0.595] | [0.135; 0.613] |
| 80% CI | [0.190; 0.581] | [0.144; 0.442] | [0.175; 0.472] |
| P-value for Hazard Ratio | 0.0115 | 0.0017 | 0.0013 |
| Unadjusted Analysis (treatment group only) | | | |
| Hazard Ratio (relative to Placebo) | 0.462 | 0.395 | 0.426 |
| 95% CI | [0.215; 0.991] | [0.183; 0.853] | [0.221; 0.823] |
| 80% CI | [0.280; 0.761] | [0.239; 0.654] | [0.277; 0.655] |
| P-value for Hazard Ratio | 0.0474 | 0.0181 | 0.0111 |
| Adjusted analysis (alternative Cox PH model) [b] | | | |
| Hazard Ratio (relative to Placebo) | 0.400 | 0.361 | 0.378 |
| 95% CI | [0.177; 0.902] | [0.165; 0.789] | [0.190; 0.752] |
| 80% CI | [0.235; 0.681] | [0.217; 0.602] | [0.241; 0.593] |
| P-value for Hazard Ratio | 0.0272 | 0.0106 | 0.0056 |
| Adjusted analysis (alternative Cox PH model) [c] | | | |
| Hazard Ratio (relative to Placebo) | 0.400 | 0.356 | 0.375 |
| 95% CI | [0.178; 0.899] | [0.163; 0.778] | [0.189; 0.746] |
| 80% CI | [0.235; 0.679] | [0.213; 0.594] | [0.239; 0.588] |
| P-value for Hazard Ratio | 0.0265 | 0.0096 | 0.0051 |

Notes:
PFS is defined as the time from the randomization date to the date of the first objective documentation of disease progression or death resulting from any cause, whichever comes first.
[a] Stratified log-rank and stratified Cox PH were stratified by best response to prior therapy (CR, PR, SD vs PD) and histology subtype (squamous vs non-squamous).
[b] The model included treatment and stratification factors (best response to prior therapy [CR, PR, SD vs PD] and histology subtype [adenocarcinoma vs non-adenocarcinoma]) as covariates.
[c] The model included treatment and stratification factors (best response to prior therapy [CR, PR, SD vs PD] and histology subtype [squamous vs non-squamous]) as covariates.

Example 4—Overall Survival in Subjects with Tumors Expressing High HRG Levels

Figure 5:
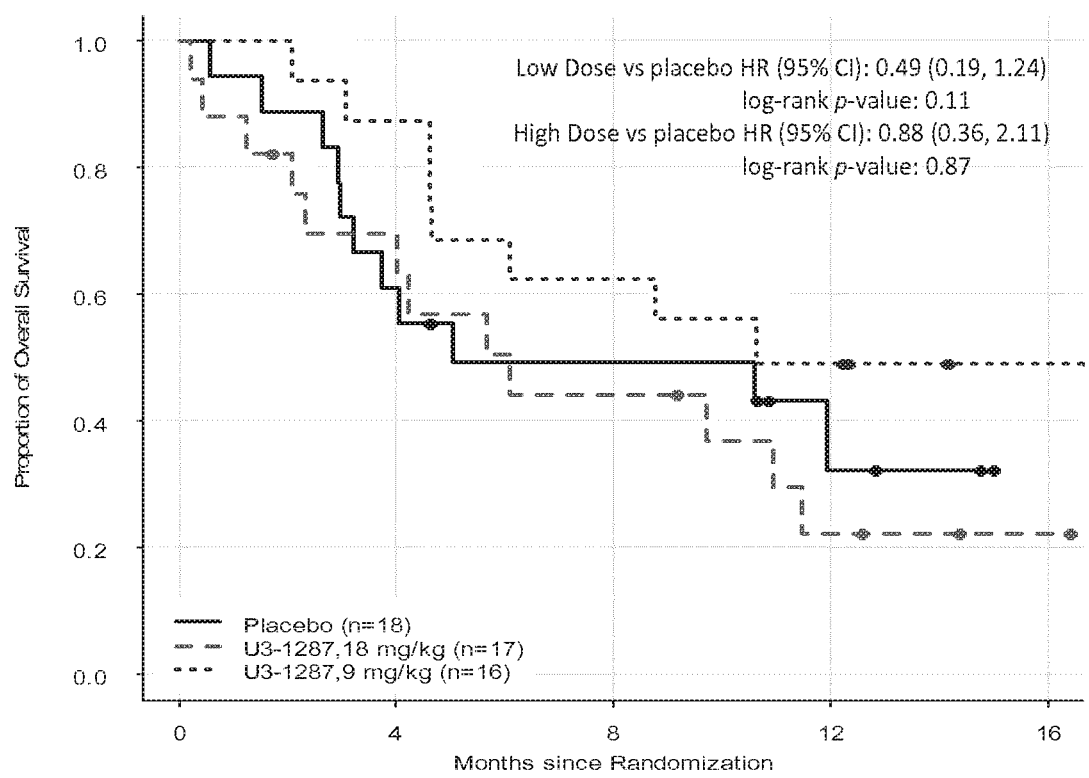
FIG. 5 depicts overall survival (showing high- and low-dose patritumab+erlotinib vs. placebo+erlitonib) for subjects from the study in Example 4 assessed as having high HRG gene expression at an mRNA level.
Figure 6:
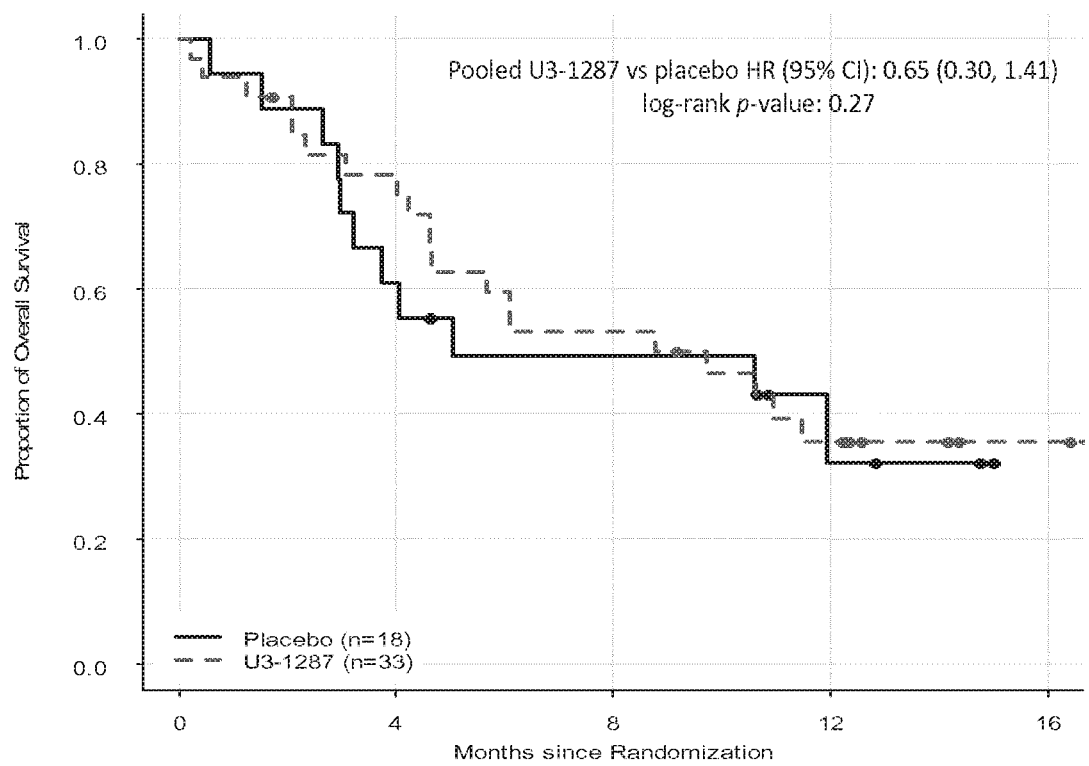
FIG. 6 depicts overall survival (showing pooled patritumab+erlotinib vs. placebo+erlitonib) for subjects from the study in Example 4 assessed as having high HRG gene expression at an mRNA level.

Preliminary OS results in the subset of subjects with tumors expressing high levels of HRG at an mRNA level, defined as dCt<3.9, are presented in Table 12 and Table 13, and in FIG. 5 (showing high- and low-dose patritumab+erlotinib vs. placebo+erlitonib) and FIG. 6 (showing pooled patritumab+erlotinib vs. placebo+erlitonib).

TABLE 12

Analysis of Overall Survival in Subjects with Tumors Expressing High HRG Levels

|  | Placebo + erlotinib (N = 18) | 18 mg/kg + erlotinib (N = 17) | 9 mg/kg + erlotinib (N = 16) | Combined (N = 33) |
|---|---|---|---|---|
| Subjects (%) with events | 11 (61.1%) | 12 (70.6%) | 9 (56.3%) | 21 (63.6%) |
| Subjects (%) without events (censored) | 7 38.9%) | 5 (29.4%) | 7 (43.8%) | 12 (36.4%) |
| Time to event (months) [a] | | | | |
| Median | 5.0 | 6.1 | 10.6 | 9.7 |
| 95% CI for Median | [3.0; NA] | [2.1; 11.5] | [4.6; NA] | [4.6; 17.4] |
| OS Rate at 6 Months (%) | 49.4% | 50.7% | 68.8% | 59.6% |
| 95% CI | [25.2; 69.7] | [25.1; 71.6] | [40.5; 85.6] | [40.7; 74.2] |
| OS Rate at 9 Months (%) | 49.4% | 44.3% | 56.3% | 50.2% |

TABLE 12-continued

Analysis of Overall Survival in Subjects with Tumors Expressing High HRG Levels

|  | Placebo + erlotinib (N = 18) | 18 mg/kg + erlotinib (N = 17) | 9 mg/kg + erlotinib (N = 16) | Combined (N = 33) |
| --- | --- | --- | --- | --- |
| 95% CI | [25.2; 69.7] | [20.2; 66.1] | [29.5; 76.2 | [32.0; 65,8] |
| OS Rate at 1 Year (%) | 32.4% | 22.2% | 49.2% | 35.8% |
| 95% CI | [10.5; 57.0] | [5.7; 45.3] | [23.6; 70.6 | [19.5; 52.5] |
| Stratified Logrank P-Value [b] |  | 0.8698 | 0.1082 | 0.2707 |
| Stratified Analysis [b] | | | | |
| Hazard Ratio (relative to Placebo) |  | 0.875 | 0.487 | 0.647 |
| 95% CI |  | [0.363; 2.111] | [0.192; 1.239] | [0.297; 1.411] |
| 80% CI |  | [0.492; 1.556] | [0.265; 0.897] | [0.389; 1.078] |
| P-value for Hazard Ratio |  | 0.7661 | 0.1311 | 0.2742 |

Notes:
OS is defined as the time from the randomization date to the date of death.
[a] Kaplan-Meier Estimate.
CI for median was computed using the Brookmeyer-Crowley method.
[b] Stratified log-rank and stratified Cox PH were stratified by best response to prior therapy (CR, PR, SD vs PD) and histology subtype (adenocarcinoma vs non-adenocarcinoma).

TABLE 13

Supportive Analysis of Overall Survival in Subjects with Tumors Expressing High HRG Levels

|  | 1.8 mg/kg + erlotinib (N = 17) | 9 mg/kg + erlotinib (N = 16) | Doses Combined (N = 33) |
| --- | --- | --- | --- |
| Logrank P-value (unstratified) | 0.5909 | 0.3077 | 0.7579 |
| Stratified Logrank P-Value [a] | 0.8302 | 0.1744 | 0.3139 |
| Stratified Analysis [a] | | | |
| Hazard Ratio (relative to Placebo) | 0.923 | 0.499 | 0.674 |
| 95% CI | [0.386; 2.207] | [0.197; 1.266] | [0.311; 1.459] |
| 80% CI | [0.522; 1.632] | [0.271; 0.917] | [0.407; 1.117] |
| P-value for Hazard Ratio | 0.8563 | 0.1435 | 0.3167 |
| Unadjusted Analysis (treatment group only) | | | |
| Hazard Ratio (relative to Placebo) | 1.254 | 0.671 | 0.892 |
| 95% CI | [0.552; 2.846] | [0.249; 1.549] | [0.427; 1.866] |
| 80% CI | [0.733; 2.143] | [0.342; 1.129] | [0.551; 1.445] |
| P-value for Hazard Ratio | 0.5890 | 0.3073 | 0.7617 |
| Adjusted analysis (alternative Cox PH model) [b] | | | |
| Hazard Ratio (relative to Placebo) | 0.918 | 0.557 | 0.716 |
| 95% CI | [0.388; 2.173] | [0.222; 1.398] | [0.334; 1.534] |
| 80% CI | [0.523; 1.613] | [0.305; 1.017] | [0.435; 1.178] |
| P-value for Hazard Ratio | 0.8458 | 0.2126 | 0.3901 |
| Adjusted analysis (alternative Cox PH model) [c] | | | |
| Hazard Ratio (relative to Placebo) | 0.933 | 0.577 | 0.736 |
| 95% CI | [0.395; 2.203] | [0.230; 1.446] | [0.345; 1.571] |
| 80% CI | [0.532; 1.637] | [0.316; 1.052] | [0.449; 1.209] |
| P-value for Hazard Ratio | 0.8747 | 0.2407 | 0.4286 |

Notes:
OS is defined as the time from the randomization date to the date of death
[a] Stratified tog-rank and stratified Cox PH were stratified by best response to prior therapy (CR, PR, SD vs PD) and histology subtype (squamous vs non-squamous).
[b] The model included treatment and stratification factors (best response to prior therapy [CR, PR, SD vs PD] and histology subtype [adenocarcinoma vs non-adenocarcinoma]) as covariates.
[c] The model included treatment and stratification factors (best response to prior therapy [CR, PR, SD vs PD] and histology subtype [squamous vs non-squamous]) as covariates.

Example 5—Objective Response Rate (ORR) and Disease Control Rate (DCR) in Subjects with Tumors Expressing High HRG Levels Subjects with tumors expressing high levels of HRG in the low-dose patritumab plus erlotinib group trended toward an improvement in objective response relative to placebo: 4 (25.0%) subjects in the low-dose group responded, as compared to 1 (5.6%) subject in the placebo group. No subject with a tumor expressing high levels of HRG in the high-dose group achieved CR or PR. Given the very small numbers, no conclusions can be drawn.

Among subjects with tumors expressing high levels of HRG, there were significant treatment differences in disease control rate in both patritumab plus erlotinib groups relative to the erlotinib plus placebo group. Disease control was achieved in 4 (22.2%) subjects in the placebo plus erlotinib group, as compared to 10 (62.5%; p=0.0068) subjects and 9 (52.9%; p=0.0129) subjects in the 9 mg/kg patritumab plus erlotinib and 18 mg/kg patritumab plus erlotinib groups, respectively.

Example 6—Efficacy in Subjects with Tumors Expressing Low HRG Levels

Figure 7:
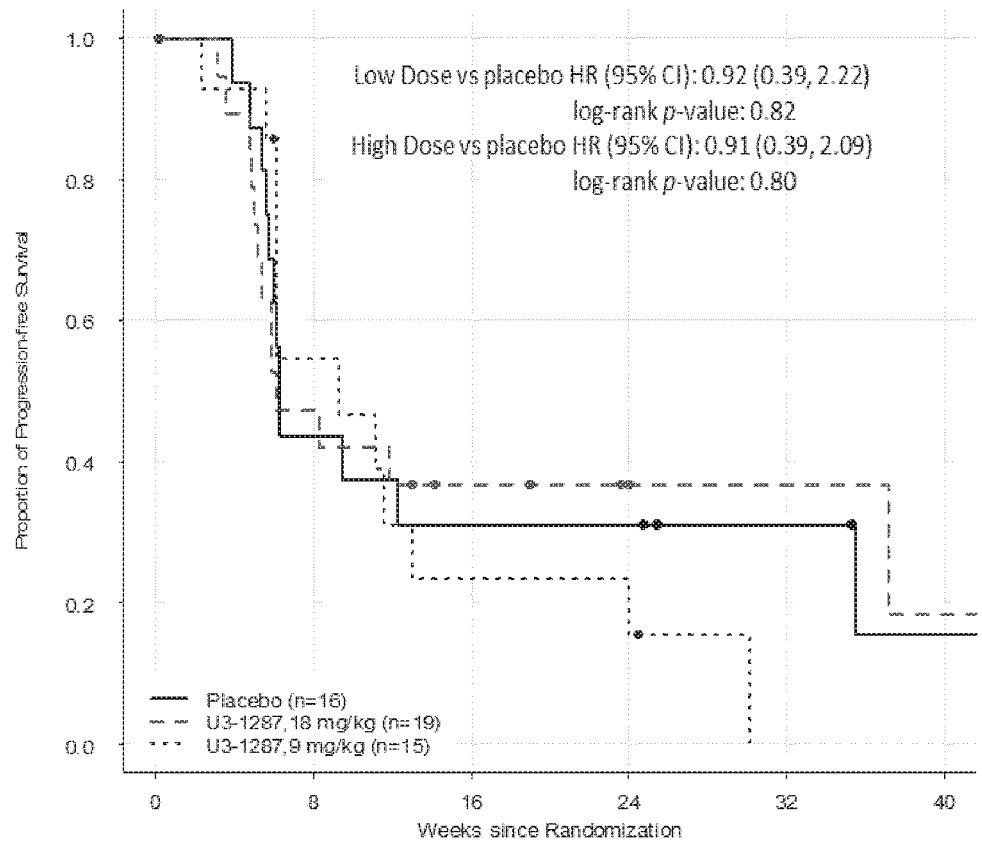
FIG. 7 depicts progression free survival (showing high- and low-dose patritumab+erlotinib vs. placebo+erlitonib) for subjects from the study in Example 6 assessed as having low HRG gene expression at an mRNA level.
Figure 8:
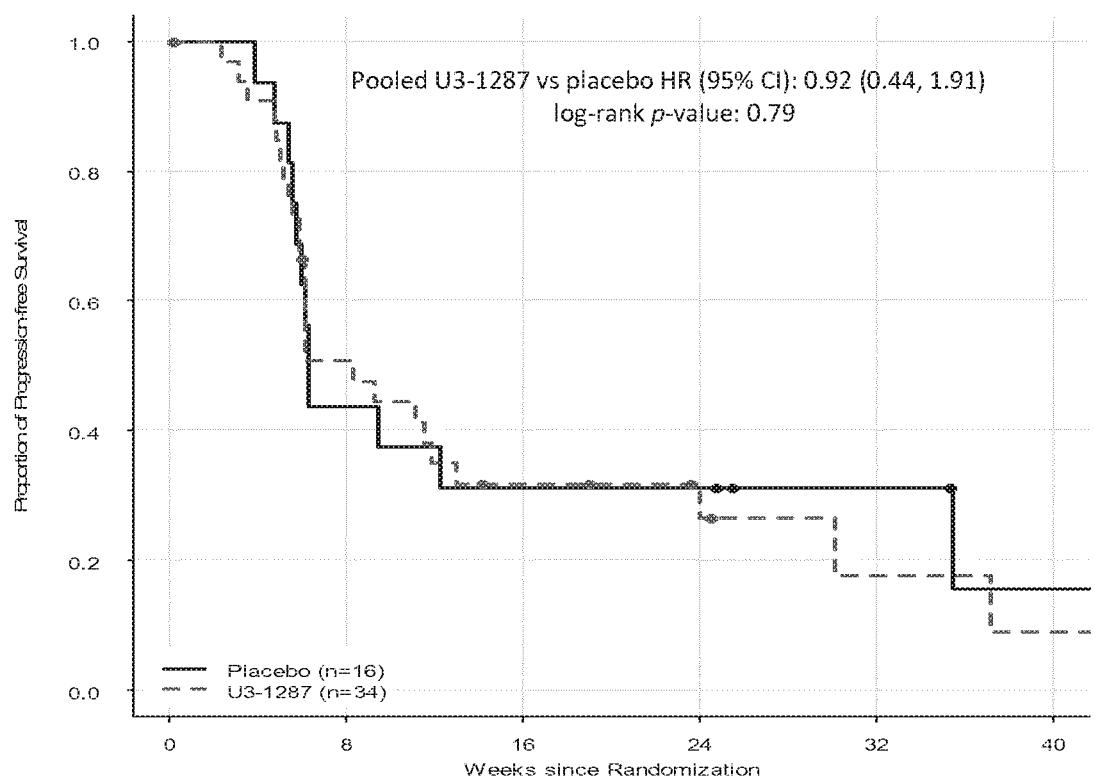
FIG. 8 depicts progression free survival (showing pooled patritumab+erlotinib vs. placebo+erlitonib) for subjects from the study in Example 6 assessed as having low HRG gene expression at an mRNA level.
Figure 9:
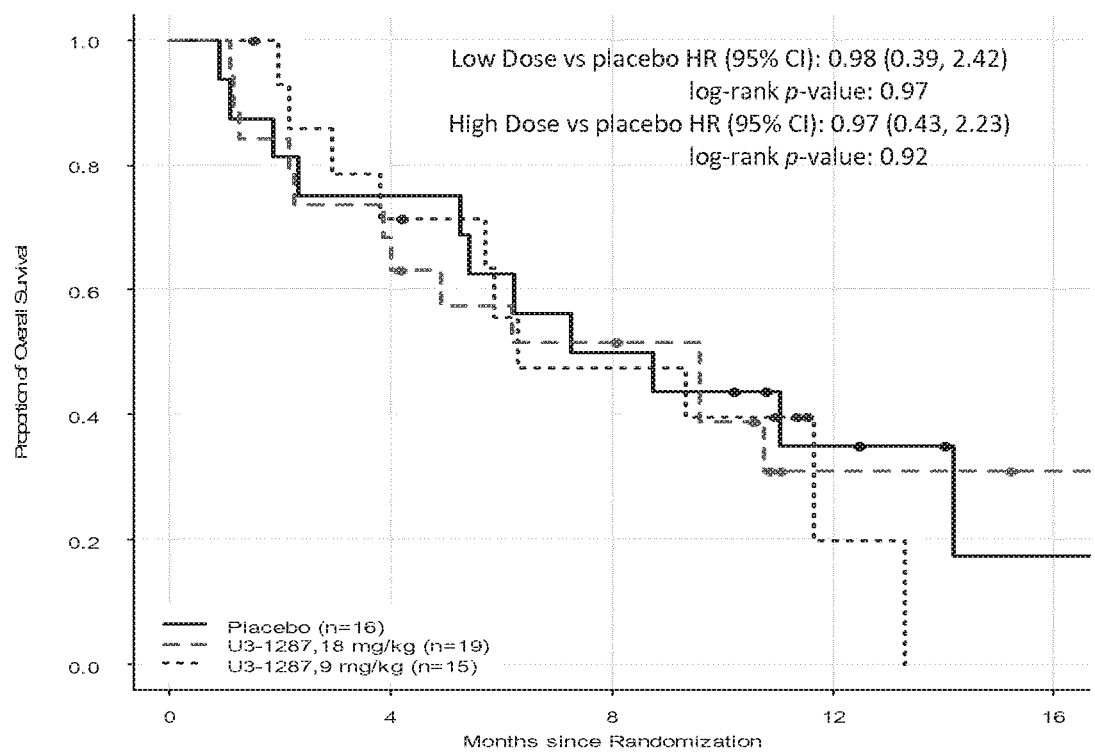
FIG. 9 depicts overall survival (showing high- and low-dose patritumab+erlotinib vs. placebo+erlitonib) for subjects from the study in Example 6 assessed as having low HRG gene expression at an mRNA level.
Figure 10:
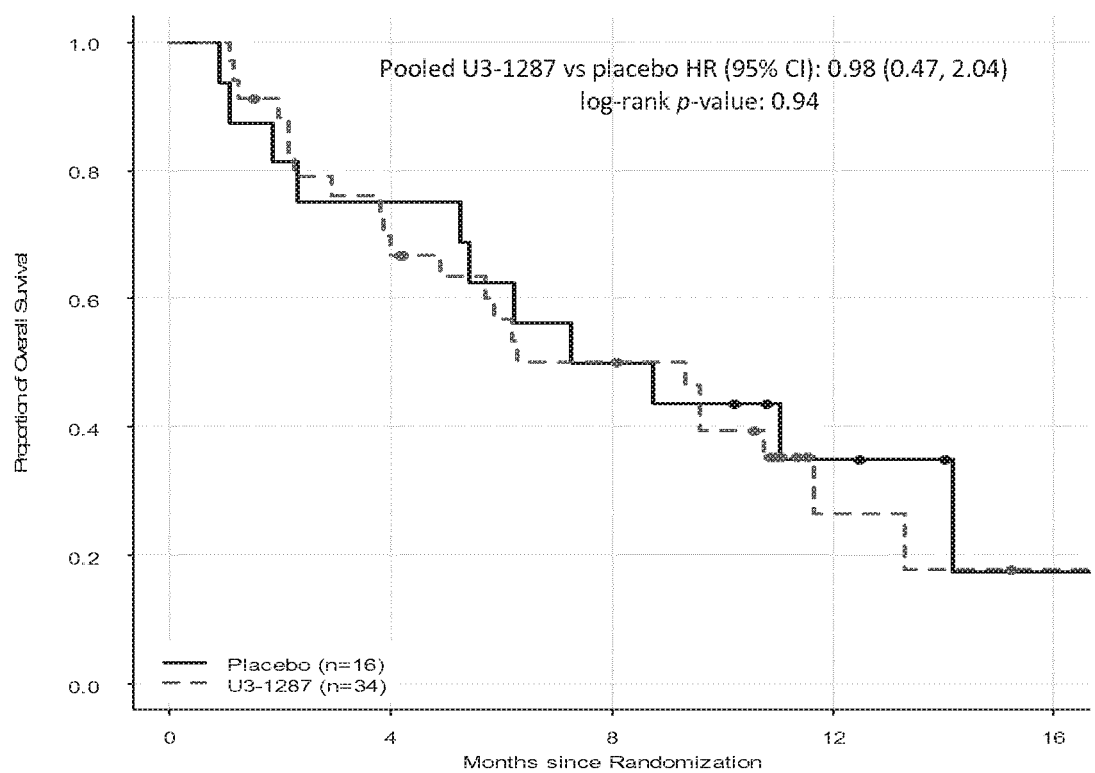
FIG. 10 depicts overall survival (showing pooled patritumab+erlotinib vs. placebo+erlitonib) for subjects from the study in Example 6 assessed as having low HRG gene expression at an mRNA level.

In contrast with subjects whose tumors expressed high levels of HRG, subjects with tumors expressing low levels of HRG showed no clear treatment difference in PFS and OS. Ad-hoc subgroup analysis of PFS and OS for subjects with tumors expressing low levels of HRG at an mRNA level, defined as dCt>3.9, are presented in Table 14 and Table 15. Kaplan-Meier estimates of PFS in subjects with tumors expressing low HRG levels are presented in FIG. 7 (showing high- and low-dose patritumab+erlotinib vs. placebo+erlitonib) and FIG. 8 (showing pooled patritumab+erlotinib vs. placebo+erlitonib). Kaplan-Meier estimates of OS in subjects with tumors expressing low HRG levels are presented in FIG. 9 (showing high- and low-dose patritumab+erlotinib vs. placebo+erlitonib) and FIG. 10 (showing pooled patritumab+erlotinib vs. placebo+erlitonib).

TABLE 14

Analysis of Progression-Free Survival in Subjects with Tumors Expressing Low HRG Levels

|  | Placebo + erlotinib (N = 16) | 18 mg/kg + erlotinib (N = 19) | 9 mg/kg + erlotinib (N = 15) | Doses Combined (N = 34) |
|---|---|---|---|---|
| Subjects % with events | 13 (81.3%) | 13 (68.4%) | 12 (80.0%) | 25 (73.5%) |
| Subjects (%) without events (censored) | 3 (18.8%) | 6 (31.6%) | 3 (20.0%) | 9 (26.5%) |
| Time to event (months) [a] | | | | |
| Median | 1.4 | 1.4 | 2.1 | 1.9 |
| 95% CI for Median | [1.3; 8.1] | [1.1; 8.5] | [1.4; 3.0] | [1.3; 3.0] |
| Stratified Logrank P-Value [b] | | 0.8025 | 0.8192 | 0.7876 |
| Stratified Analysis [b] | | | | |
| Hazard Ratio (relative to Placebo) | | 0.908 | 0.924 | 0.915 |
| 95% CI | | [0.394; 2.091] | [0.385; 2.219] | [0.439; 1.908] |
| 80% CI | | [0.526; 1.567] | [0.521; 1.639] | [0.566; 1.480] |
| P-value for Hazard Ratio | | 0.8204 | 0.8599 | 0.8132 |

Notes:
PFS is defined as the time from the randomization date to the date of the first objective documentation of disease progression or death resulting from any cause, whichever comes first.
[a] Kaplan-Meier Estimate. CI for median was computed using the Brookmeyer-Crowley method.
[b] Stratified log-rank and stratified Cox PH were stratified by best response to prior therapy (CR, PR, SD vs PD) and histology subtype (adenocarcinoma vs non-adenocarcinoma).

Example 7A—HRG is Both a Prognostic and a Predictive Biomarker

TABLE 15

Analysis of Overall Survival in Subjects with Tumors Expressing Low HRG Levels

|  | Placebo + erlotinib (N = 16) | 18 mg/kg erlotinib (N = 19) | 9 mg/kg + erlotinib (N = 15) | Doses Combined (N = 34) |
|---|---|---|---|---|
| Subjects (%) with events | 11 (68.8%) | 12 (63.2%) | 10 (66.7%) | 22 (64.7%) |
| Subjects (%) without events (censored) | 5 (31.3%) | 7 (36.8%) | 5 (33.3%) | 12 (35.3%) |
| Time to event (months) [a] | | | | |
| Median | 8.0 | 9.6 | 6.3 | 9.3 |
| 95% CI for Median | [2.3; 14.2] | [2.3; NA] | [2.9; 13.3] | [4.0; 11.7] |
| Stratified Logrank P-Value [b] | | 0.9165 | 0.9713 | 0.9402 |
| Stratified Analysis [b] | | | | |
| Hazard Ratio (relative to Placebo) | | 0.974 | 0.978 | 0.976 |
| 95% CI | | [0.426; 2.229] | [0.395; 2.424] | [0.467; 2.040] |
| 80% CI | | [0.567; 1.674] | [0.541; 1.771] | [0.603; 1.580] |
| P-value for Hazard Ratio | | 0.9506 | 0.9625 | 0.9484 |

Notes:
OS is defined as the time from the randomization date to the date of death.
[a] Kaplan-Meier Estimate.
CI for median was computed using the Brookmeyer-Crowley method.
[b] Stratified log-rank and stratified Cox PH were stratified by best response to prior therapy (CR, PR, SD vs PD) and histology subtype (adenocareinorna vs non-adenocarcinoma).

Figure 11:
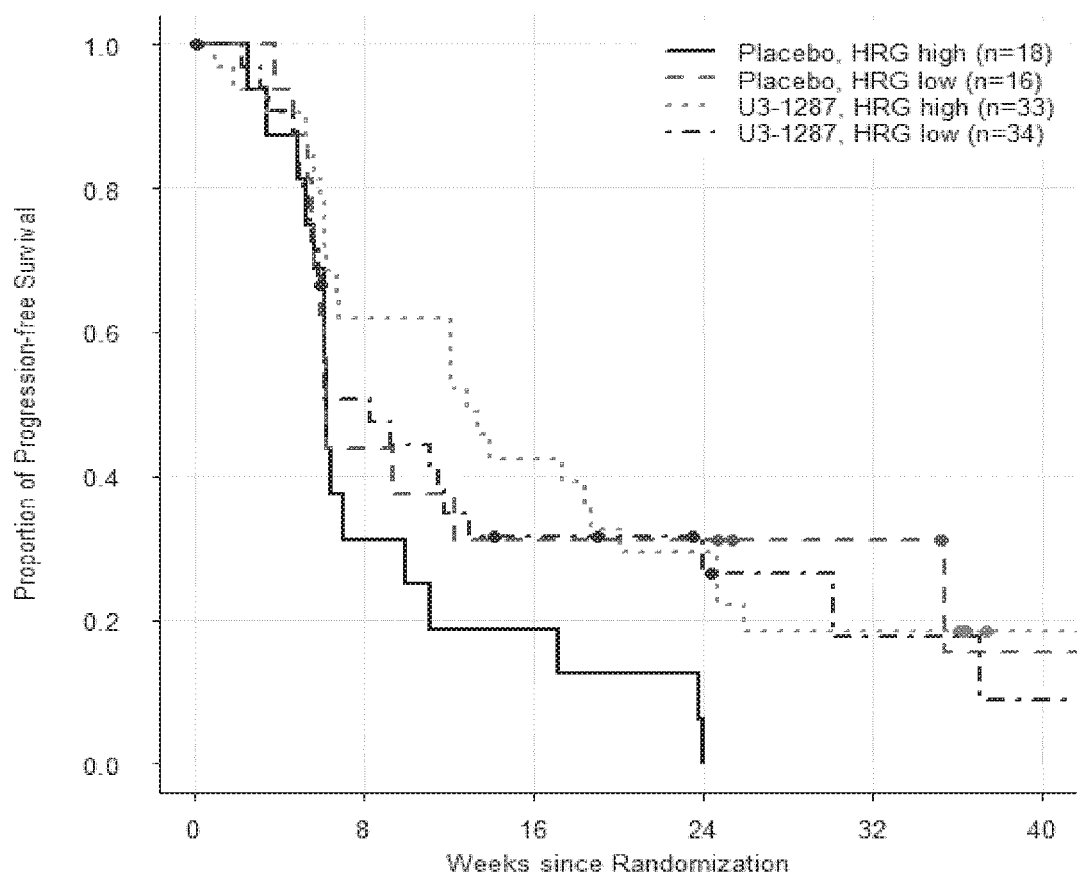
FIG. 11 depicts progression free survival (showing high- and low-dose patritumab+erlotinib vs. placebo+erlitonib) for subjects from the study in Example 7 assessed as having high HRG gene expression at an mRNA level and for subjects assessed as having low HRG gene expression at an mRNA level.

An exploratory analysis of treatment effect as judged by PFS was performed for the HRG high and low groups versus their comparative placebo groups. As shown in FIG. 11, the analysis suggested that HRG high is a negative prognostic factor for single agent erlotinib treatment and a positive predictive factor for clinical benefit from the addition of patritumab.

Based on blinded samples with respect to treatment group and clinical outcomes, an HRG high subject was defined as the subject with mRNA expression of HRG in the tumor with delta Ct value<3.9 (median), and key efficacy analyses were performed for HRG high group based on such pre-specified definition. Additional ad-hoc exploratory analyses were performed to determine the cut-offs for HRG expression.

A post-hoc analysis used a log likelihood approach for cut-off values based on PFS. Log partial likelihoods for stratified Cox proportional hazards model were calculated for both HRG high and low groups based on a variety of possible HRG cut-off values.

Example 7B—Determination of Optimal Cut-Off for HRG mRNA Expression

Figure 12:
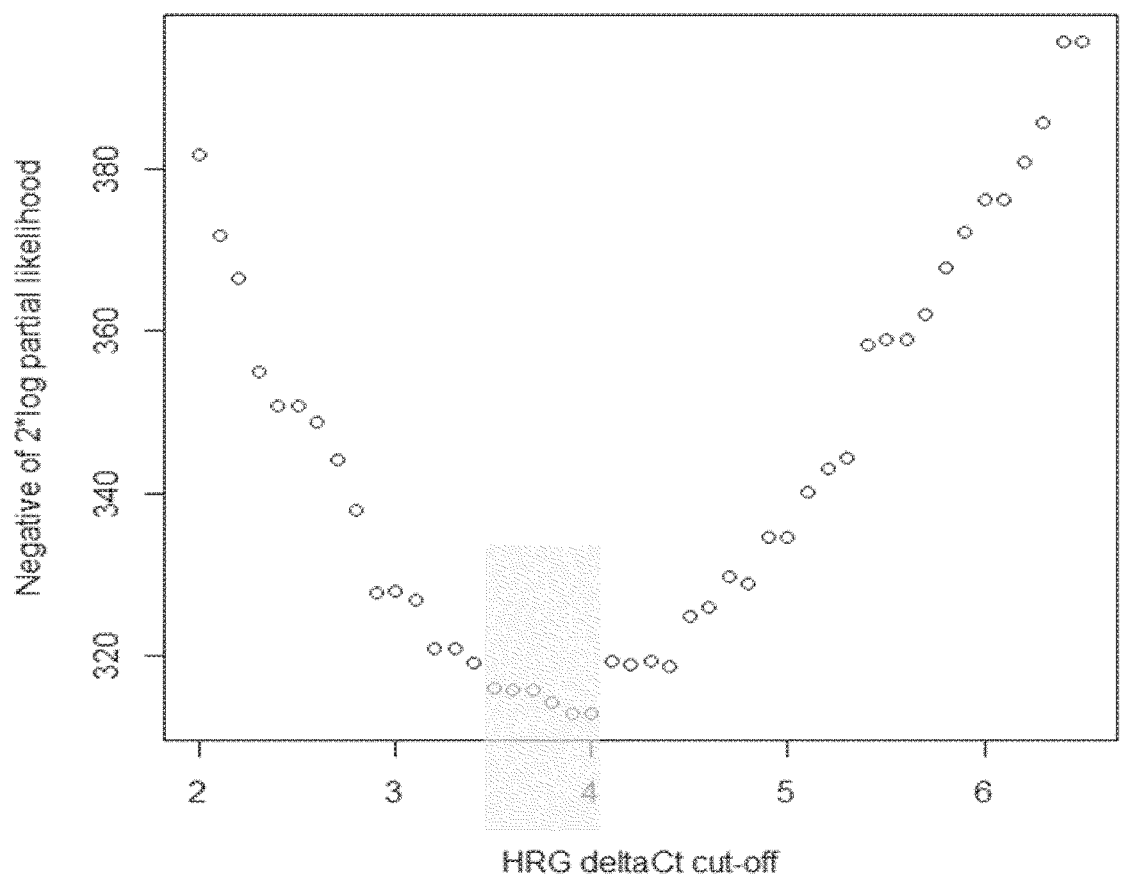
FIG. 12 depicts optimized cut-off values for high HRG and low HRG groups.

Based on the plot of the sum of negative log partial likelihoods versus cut-off value, the optimized maximum likelihood cut-off value fell within the range of 3.5 to 4.0, as shown in FIG. 12.

Data was also used to calculate hazard ratios between the pooled dose of patritumab and placebo based on several potential cut-off values for delta Ct. These hazard ratios are shown in Table 16. Lower dCt values represent higher HRG mRNA expression. It appears that higher HRG expression was associated with greater clinical benefit in terms of PFS. Lowering the cutoff from 3.9 to 3.0 results in additional improvement in the average benefit as judged by the hazard ratio without dramatically lowering the size of the HRG high population.

TABLE 16

Hazard ratio and p-values for PFS in the HRC high group as a function of cutoff

| Cut-off for delta Ct | n (#events) | HR (pooled dose vs placebo) | Log-rank p-value |
|---|---|---|---|
| 2.7 (first quartile) | 24 (18) | 0.180 | 0.0039 |
| 3.0 | 33 (24) | 0.177 | 0.0009 |
| 3.5 | 46 (36) | 0.283 | 0.0009 |
| 3.9 (median) | 51 (41) | 0.324 | 0.0013 |
| 4.5 | 65 (50) | 0.490 | 0.0190 |
| 5.0 (third quartile) | 76 (58) | 0.561 | 0.0429 |

Example 8—Treatment Efficacy in Subjects with Tumors Expressing High HRG Levels and EGFR Wild Type In the HRG high group, there were 2 subjects with a sensitizing mutation (1 on placebo and 1 on low dose); 21 subjects with wild type (9 on placebo, 7 on low dose, and 5 on high dose) and 28 subjects with unknown/indeterminate mutation status (8 on placebo, 12 on low dose, and 8 on high dose) (Table 17).

Figure 13:
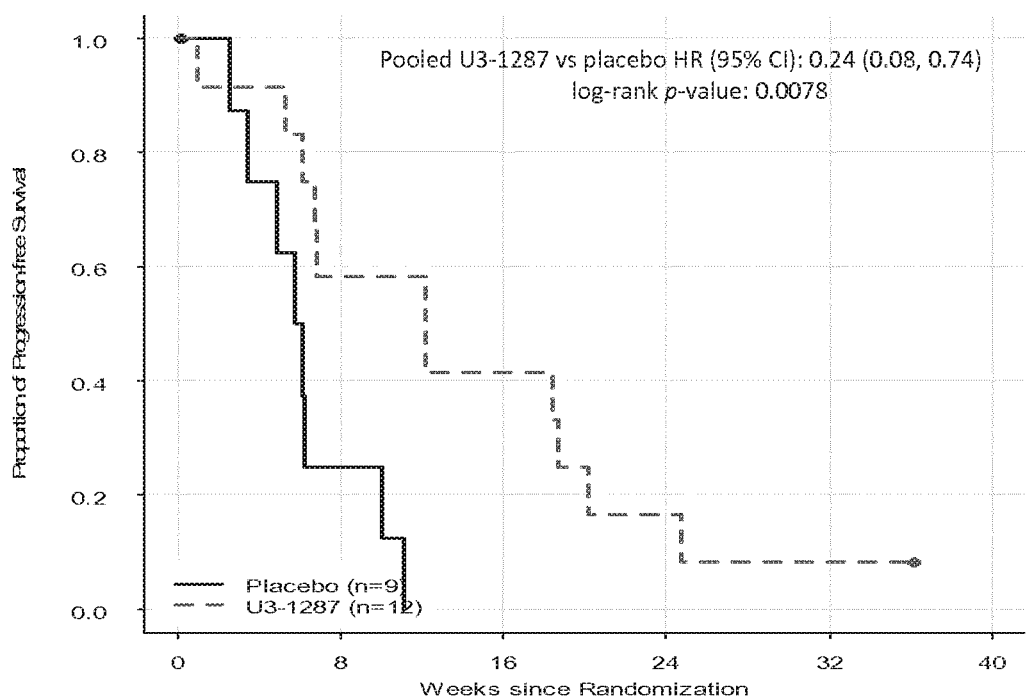
FIG. 13 depicts progression free survival for subjects from the study in Example 8 assessed as having high HRG gene expression at an mRNA level and EGFR wild type.

Ad-hoc subgroup analysis of PFS for subjects with tumors expressing high levels of HRG and EGFR wild type are presented in Table 17 based on un-stratified analysis and Kaplan-Meier estimates of PFS is presented in FIG. 13 (pooled patritumab+erlotinib vs. placebo+erlotinib). An analysis of HRG high, EGFR wild type subjects showed that the clinical benefit with respect to PFS was maintained with pooled dose vs placebo: HR 0.24 (95% CI: 0.08, 0.74; P-value=0.008) based on un-stratified analysis.

TABLE 17

Analysis of Progression-Free Survival in Subjects with Tumors Expressing High HRG Levels and EGFR Wild Type

|  | Placebo + erlotinib (N = 9) | 18 mg/kg + erlotinib (N = 5) | 9 mg/kg + erlotinib (N = 7) | Doses Combined (N = 12) |
|---|---|---|---|---|
| Subjects (%) with events | 8 (88.9%) | 5 (100.0%) | 6 (85.7%) | 11 (91.7%) |
| Subjects (%) without events (censored) | 1 (11.1%) | 0 | 1 (14.3%) | 1 (8.3%) |
| Time to event (months) [a] | | | | |
| Median | 1.4 | 2.8 | 2.8 | 2.8 |
| 95% CI for Median | [0.6; 2.3] | [0.2; 4.3] | [1.4; 5.7] | [1.2; 4.6] |
| Unstratified Logrank P-Value | | 0.0913 | 0.0107 | 0.0078 |
| Unstratified Analysis | | | | |
| Hazard Ratio (relative to Placebo) | | 0.361 | 0.167 | 0.237 |
| 95% CI | | [0.099; 1.317] | [0.043; 0.647] | [0.075; 0.744] |
| 80% CI | | [0.155; 0.842] | [0.069; 0.405] | [0.112; 0.500] |
| P-value for Hazard Ratio | | 0.123 | 0.0096 | 0.0137 |

Notes:

PFS is defined as the time from the randomization date to the date of the first objective documentation of disease progression or death resulting from any cause, whichever comes first.

[a] Kaplan-Meier Estimate.

CI for median was computed using the Brookmeyer-Crowley method.

Example 9—Biomarker Identification

The HRG biomarker was identified by analysing the anti-tumor activity of the anti-HER3 antibody U3-1287 on various human cancer xenografts in vivo and analysis of the expression of HRG of these cell lines in vitro. Human tumor cell lines of various indications were grown as xenografts in mice and treated with the anti-HER3 antibody U3-1287 for several weeks. Inhibition of tumor growth was analysed by comparing the tumor volumes of control mice and mice treated with U3-1287. Human tumor cell lines were grown in vitro and analysed for HRG RNA expression by PCR. The results of this analysis are shown in Table 18. Basal activity of HER3 as measured by Western blotting did not correlate with in vivo efficacy of U3-1287, predominantly in FISH positive breast cancer models. In contrast, expression of HRG correlated very well with in vivo efficacy of U3-1287, as seen for 15 of the 17 models analyzed.

TABLE 18

Retrospective in vitro analysis of cell lines used for in vivo xenografts

| Cell Line | Indication | HER (WB) | Phospho HER3 (WB) | HRG (PCR) | In vivo efficacy (SA) | Correlation |
|---|---|---|---|---|---|---|
| Sum225 | BC FISH + ve | + | + | − | No | Yes |
| MDA-MB453 | BC FISH + ve | + | + | − | No | Yes |
| BT474 | BC FISH + ve | + | + | − | No | Yes |
| HCC 1569 | BC FISH + ve | + | + | − | No | Yes |
| ZR75-1 | BC FISH + ve | + | − | − | No | Yes |
| MCF-7 | BC FISH + ve | + | − | − | No | Yes |
| T47D | BC FISH + ve | + | + | − | No | Yes |
| NCI-H441 | NSCLC | + | + | − | No | Yes |
| A549 | NSCLC | + | + | + | Yes | Yes |
| Calu-3 | NSCLC | + | + | + | Yes | Yes |
| NC-H1975 | NSCLC | + | + | + | Yes | Yes |
| A375 | Melanoma | + | − | − | No | Yes |
| HT-144 | Melanoma | + | − | + | No | Yes |
| HT-29 | Colon | + | + | − | Yes | No |
| MKN-45 | Gastric | + | + | − | Yes | No |
| BxPC3 | Pancreas | + | + | + | Yes | Yes |
| FaDu | Head&Neck | + | + | + | Yes | Yes |

Figure 14:
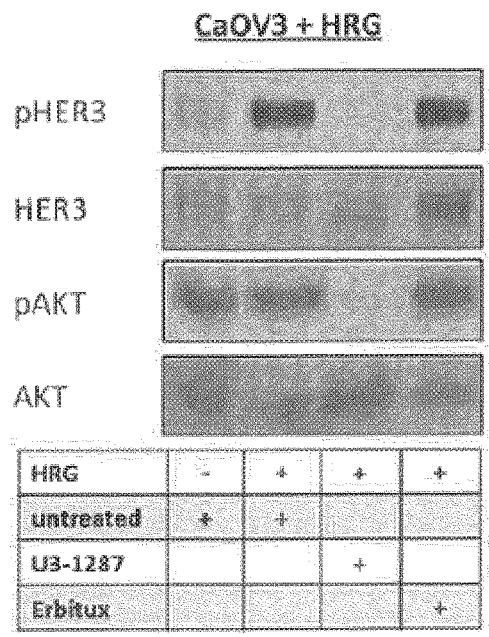
FIG. 14 depicts efficacy determined in vitro by measuring reduction of phospho-HER3 and phospho-AKT levels by Western blotting.
Figure 14:

U3-1287 efficacy was determined in vitro by measuring reduction of phospho-HER3 and phospho-AKT levels. Basal HER3 phosphorylation could be blocked in cell lines that endogenously express heregulin (A549) as well as in cells that do not have basal HER3 activation but were stimulated with exogenous heregulin (CaOV3). U3-1287 efficacy results are shown in FIG. 14.

Figure 15:
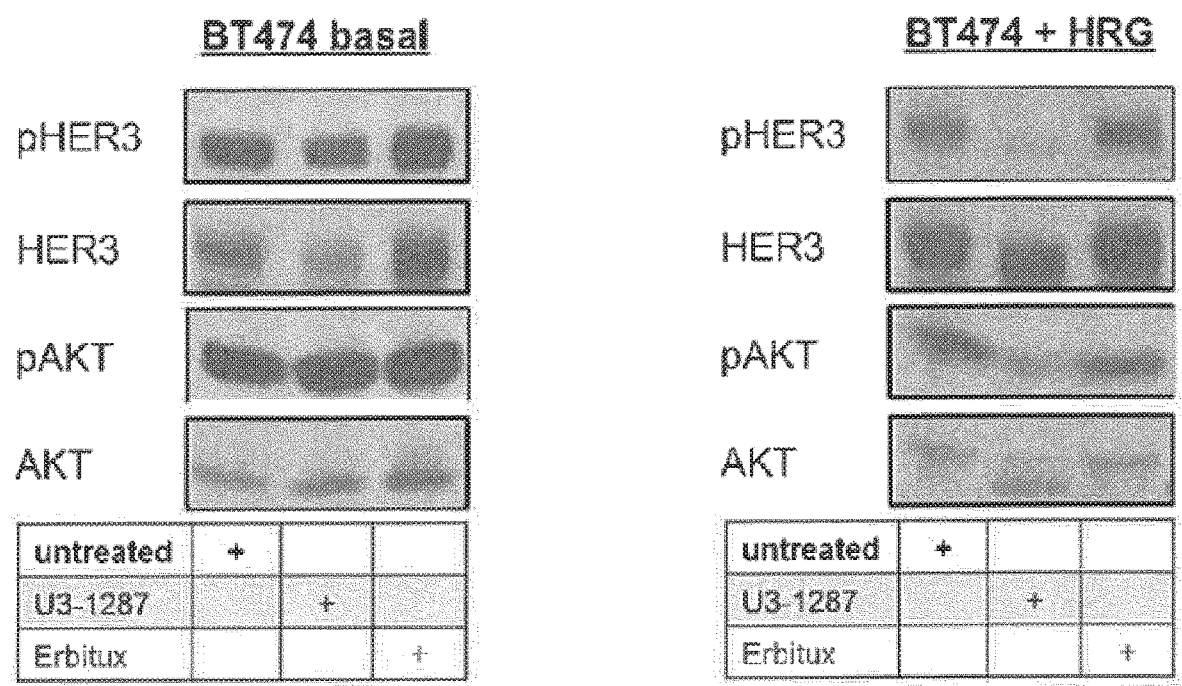
FIG. 15 depicts Western blots showing that U3-1287 can block ligand-dependent basal HER3 phosphorylation.

Unexpectedly, cells that have basal HER3 phosphorylation but do not express heregulin showed no efficacy upon U3-1287 treatment (BT474 basal) and even more surprisingly, this could be overcome by exogenously added heregulin (BT474+HRG), as shown in FIG. 15.

INCORPORATION BY REFERENCE

The entire disclosure of each of the patent documents and scientific articles cited herein is incorporated by reference for all purposes.

APPENDIX A

The below table (Table A1) shows unblinded data from Example 1. In the table, U3-1287 corresponds to patritumab.

| Patient # | Cancer Stage | Prior Cancer Therapy | HRG deltaCt (mRNA) | Treatment | PFS* (days) | OS* (days) | Best Response |
|---|---|---|---|---|---|---|---|
| 1 | IV | CARBOPLATIN + PEMETREXED | 4.64 | U3-1287 18 mg/kg + Erlotinib | 41 | 118 | PD |
| 2 | IV | CARBOPLATIN + OTHER: ETOPOSIDE; CARBOPLATIN + DOCETAXEL; VINORELBINE | 5.35 | U3-1287 9 mg/kg + Erlotinib | 78 | 192 | SD |
| 3 | IV | BEVACIZUMAB + CARBOPLATIN + PEMETREXED | 4.8 | U3-1287 9 mg/kg + Erlotinib | 1(c) | 46(c) | NE |

-continued

| Patient # | Cancer Stage | Prior Cancer Therapy | HRG deltaCt (mRNA) | Treatment | PFS* (days) | OS* (days) | Best Response |
|---|---|---|---|---|---|---|---|
| 4 | IV | CARBOPLATIN + PACLITAXEL + BEVACIZUMAB | 3.14 | U3-1287 18 mg/kg + Erlotinib | 37 | 185 | PD |
| 5 | IV | CISPLATIN + PEMETREXED; CARBOPLATIN + PACLITAXEL + BEVACIZUMAB | 3.92 | Placebo + Erlotinib | 402 | 562(c) | PR |
| 6 | IV | CARBOPLATIN + PACLITAXEL + BEVACIZUMAB | 2.52 | Placebo + Erlotinib | 37 | 90 | PD |
| 7 | IV | CARBOPLATIN + PACLITAXEL | 4.61 | Placebo + Erlotinib | 40 | 190 | PD |
| 8 | IV | CARBOPLATIN + PACLITAXEL; DOCETAXEL + OTHER: BIBF1120/PLACEBO | 2.09 | U3-1287 9 mg/kg + Erlotinib | 426(c) | 641(c) | PR |
| 9 | IV | OTHER: PAZOPANIB + PEMETREXED | 5.32 | Placebo + Erlotinib | 86 | 432 | SD |
| 10 | IV | CARBOPLATIN + PACLITAXEL; PEMETREXED + OTHER: PLACEBO!!!/ (BIBF1120) | 4.82 | U3-1287 18 mg/kg + Erlotinib | 38 | 38 | NE |
| 11 | IV | CARBOPLATIN + PACLITAXEL | 4.45 | Placebo + Erlotinib | 33 | 33 | NE |
| 12 | IV | CARBOPLATIN + PACLITAXEL | 2.22 | U3-1287 9 mg/kg + Erlotinib | 98 | 531 | PR |
| 13 | IV | CARBOPLATIN + PACLITAXEL + OTHER: OMBRABULIN/ PLACEBO | 3.1 | U3-1287 18 mg/kg + Erlotinib | 182 | 499(c) | SD |
| 14 | IIIB | CARBOPLATIN + PACLITAXEL | 2 | U3-1287 9 mg/kg + Erlotinib | 94 | 430(c) | SD |
| 15 | IV | CARBOPLATIN + PACLITAXEL | 4.49 | U3-1287 9 mg/kg + Erlotinib | 43 | 66 | PD |
| 16 | IV | CARBOPLATIN + PACLITAXEL + OTHER: OMBRABULIN/ PLACEBO | 5.14 | U3-1287 18 mg/kg + Erlotinib | 260 | 463(c) | SD |
| 17 | IV | CARBOPLATIN + PACLITAXEL + OTHER: OMBRABULIN/ PLACEBO | 3.12 | U3-1287 18 mg/kg + Erlotinib | 13 | 13 | NE |
| 18 | IV | CARBOPLATIN + PEMETREXED | 0.09 | U3-1287 9 mg/kg + Erlotinib | 42 | 142 | PD |
| 19 | IV | CISPLATIN + VINORELBINE | 3.36 | U3-1287 9 mg/kg + Erlotinib | 329(c) | 510(c) | PR |
| 20 | IV | CARBOPLATIN + PACLITAXEL + OTHER: OMBRABULIN/ PLACEBO | 4.75 | U3-1287 18 mg/kg + Erlotinib | 328(c) | 524(c) | PR |
| 21 | IV | CARBOPLATIN + GEMCITABINE; DOCETAXEL | 3.07 | Placebo + Erlotinib | 44 | 114 | PD |
| 22 | IIIB | CISPLATIN + GEMCITABINE; DOCETAXEL | 2.25 | U3-1287 9 mg/kg + Erlotinib | 90 | 140 | SD |
| 23 | IV | CISPLATIN + GEMCITABINE + OTHER: SAR240550(INIPARIB = PARP1INHIBITOR); OTHER: BIBF1120(VEGFINHIBITOR) + PEMETREXED | 4.59 | U3-1287 9 mg/kg + Erlotinib | 91 | 405 | SD |
| 24 | IV | CARBOPLATIN + PACLITAXEL | 2.73 | Placebo + Erlotinib | 18 | 18 | NE |
| 25 | IV | CARBOPLATIN + PACLITAXEL | 4.35 | U3-1287 18 mg/kg + Erlotinib | 91(c) | 189 | PR |

-continued

| Patient # | Cancer Stage | Prior Cancer Therapy | HRG deltaCt (mRNA) | Treatment | PFS* (days) | OS* (days) | Best Response |
|---|---|---|---|---|---|---|---|
| 26 | IV | CARBOPLATIN + PACLITAXEL | 3.45 | U3-1287 18 mg/kg + Erlotinib | 173 | 173 | SD |
| 27 | IV | CARBOPLATIN + PACLITAXEL + OTHER: OMBRABULIN/PLACEBO | 3.89 | Placebo + Erlotinib | 49 | 89 | PD |
| 28 | IIIB | CISPLATIN + GEMCITABINE | 3.53 | U3-1287 18 mg/kg + Erlotinib | 122 | 122 | SD |
| 29 | IV | CARBOPLATIN + PACLITAXEL | 5.73 | U3-1287 18 mg/kg + Erlotinib | 133(c) | 292 | SD |
| 30 | IV | CARBOPLATIN + PACLITAXEL + OTHER: OMBRABULIN | 1.83 | U3-1287 18 mg/kg + Erlotinib | 262(c) | 349 | SD |
| 31 | IIIB | CARBOPLATIN + PACLITAXEL | 5.7 | Placebo + Erlotinib | 44 | 165 | PD |
| 32 | IV | CISPLATIN + PACLITAXEL; DOCETAXEL | 2.27 | U3-1287 18 mg/kg + Erlotinib | 24 | 382(c) | PD |
| 33 | IV | CARBOPLATIN + PACLITAXEL + OTHER: OMBRABULIN/PLACEBO | 2.77 | Placebo + Erlotinib | 45 | 98 | PD |
| 34 | IV | CARBOPLATIN + GEMCITABINE | 2.72 | Placebo + Erlotinib | 1(c) | 390(c) | SD |
| 35 | IV | CARBOPLATIN + PACLITAXEL + OTHER: OMBRABULIN/PLACEBO | 6.09 | U3-1287 9 mg/kg + Erlotinib | 43 | 60 | PD |
| 36 | IV | CISPLATIN + PACLITAXEL | 2.44 | U3-1287 18 mg/kg + Erlotinib | 44 | 63 | PD |
| 37 | IV | CISPLATIN + PEMETREXED | 3.3 | U3-1287 18 mg/kg + Erlotinib | 38 | 38 | NE |
| 38 | IV | CISPLATIN + PEMETREXED | 4.45 | U3-1287 9 mg/kg + Erlotinib | 43 | 355 | PD |
| 39 | IV | CARBOPLATIN + PEMETREXED + BEVACIZUMAB | 6.32 | Placebo + Erlotinib | 39 | 266 | PD |
| 40 | IV | CARBOPLATIN + PACLITAXEL + BEVACIZUMAB; PEMETREXED | 4.09 | Placebo + Erlotinib | 178(c) | 336 | SD |
| 41 | IV | CISPLATIN + PEMETREXED + OTHER: PANITUMUMAB | 7.13 | U3-1287 18 mg/kg + Erlotinib | 35 | 35 | NE |
| 42 | IV | BEVACIZUMAB + CARBOPLATIN + PEMETREXED | 2.29 | U3-1287 9 mg/kg + Erlotinib | 43(c) | 375(c) | PR |
| 43 | IV | CARBOPLATIN + GEMCITABINE | 2.66 | Placebo + Erlotinib | 24 | 363 | PD |
| 44 | IV | CISPLATIN + VINORELBINE | 2.98 | Placebo + Erlotinib | 1(c) | 448(c) | NE |
| 45 | IV | CARBOPLATIN + PACLITAXEL | 5.12 | U3-1287 18 mg/kg + Erlotinib | 33 | 33 | NE |
| 46 | IV | CISPLATIN + PEMETREXED | 4.15 | U3-1287 18 mg/kg + Erlotinib | 36 | 69 | PD |
| 47 | IV | CARBOPLATIN + VINORELBINE; CARBOPLATIN + PEMETREXED; OTHER: MAGRIT(VACCINATION) | 3.93 | U3-1287 18 mg/kg + Erlotinib | 34 | 292 | PD |
| 48 | IV | CARBOPLATIN + PACLITAXEL + OTHER: OMRABULINVS.PLACEBO | 5.2 | U3-1287 18 mg/kg + Erlotinib | 99(c) | 149 | SD |
| 49 | IV | CARBOPLATIN + GEMCITABINE; DOCETAXEL | 1.88 | U3-1287 9 mg/kg + Erlotinib | 47 | 93 | PD |

-continued

| Patient # | Cancer Stage | Prior Cancer Therapy | HRG deltaCt (mRNA) | Treatment | PFS* (days) | OS* (days) | Best Response |
|---|---|---|---|---|---|---|---|
| 50 | IV | CISPLATIN + PEMETREXED | 2.85 | U3-1287 9 mg/kg + Erlotinib | 48 | 64 | PD |
| 51 | IIIB | CISPLATIN + PACLITAXEL; CISPLATIN + VINORELBINE | 2.51 | U3-1287 18 mg/kg + Erlotinib | 141(c) | 296 | SD |
| 52 | IV | CISPLATIN + VINORELBINE; CARBOPLATIN + PACLITAXEL | 1.51 | Placebo + Erlotinib | 43 | 456(c) | PD |
| 53 | IV | CISPLATIN + VINORELBINE; CARBOPLATIN + PACLITAXEL | 4.66 | U3-1287 9 mg/kg + Erlotinib | 168 | 284 | SD |
| 54 | IV | CISPLATIN + PEMETREXED | 6.23 | U3-1287 18 mg/kg + Erlotinib | 43 | 122 | PD |
| 55 | IV | CISPLATIN + PEMETREXED | 5.62 | U3-1287 9 mg/kg + Erlotinib | 43 | 179 | PD |
| 56 | IV | CARBOPLATIN + GEMCITABINE; OTHER: LUCANIXVACCINE | 5.33 | U3-1287 18 mg/kg + Erlotinib | 58 | 330(c) | PD |
| 57 | IV | CISPLATIN + CARBOPLATIN + GEMCITABINE | 2.47 | U3-1287 18 mg/kg + Erlotinib | 40 | 71 | PD |
| 58 | IV | CARBOPLATIN + GEMCITABINE; PEMETREXED | 6.37 | Placebo + Erlotinib | 66 | 160 | PD |
| 59 | IV | CISPLATIN + GEMCITABINE; PEMETREXED | 4.87 | U3-1287 9 mg/kg + Erlotinib | 39 | 116 | PD |
| 60 | IV | CISPLATIN + VINORELBINE; CISPLATIN + PEMETREXED | 5.25 | U3-1287 18 mg/kg + Erlotinib | 25 | 327 | PD |
| 61 | IV | CARBOPLATIN + PEMEMETREXED | 5.96 | U3-1287 18 mg/kg + Erlotinib | 41 | 66 | PD |
| 62 | IV | CARBOPLATIN + OTHER: TAXOTERE; CARBOPLATIN + GEMCITABINE | 3.04 | Placebo + Erlotinib | 120 | 323(c) | SD |
| 63 | IV | CISPLATIN + OTHER: ETOPOSIDE | 4.46 | U3-1287 9 mg/kg + Erlotinib | 16 | 89 | PD |
| 64 | IIIB | CISPLATIN + CISPLATIN + PEMETREXED | 2.15 | U3-1287 9 mg/kg + Erlotinib | 43 | 267 | PD |
| 65 | IV | CISPLATIN + OTHER: INVESTIGATIONALDRUG + PEMETREXED; DOCETAXEL | 2.81 | U3-1287 9 mg/kg + Erlotinib | 85 | 323 | PD |
| 66 | IIIB | CARBOPLATIN + VINORELBINE; CISPLATIN + VINORELBINE | 4.4 | U3-1287 9 mg/kg + Erlotinib | 42(c) | 128(c) | SD |
| 67 | IIIB | CISPLATIN + VINORELBINE; DOCETAXEL | 4.21 | U3-1287 9 mg/kg + Erlotinib | 211 | 333(c) | SD |
| 68 | IV | CARBOPLATIN + PACLITAXEL | 3.42 | U3-1287 18 mg/kg + Erlotinib | 131 | 333 | SD |
| 69 | IV | CISPLATIN + VINORELBINE; PACLITAXEL | 0.76 | U3-1287 9 mg/kg + Erlotinib | 253(c) | 372(c) | SD |
| 70 | IIIB | CISPLATIN + GEMCITABINE | 6.99 | U3-1287 18 mg/kg + Erlotinib | 22 | 127(c) | PD |
| 71 | IV | CISPLATIN + GEMCITABINE; DOCETAXEL | 2.3 | Placebo + Erlotinib | 40 | 153 | PD |
| 72 | IV | CISPLATIN + GEMCITABINE | 2.35 | U3-1287 18 mg/kg + Erlotinib | 255(c) | 437(c) | SD |

-continued

| Patient # | Cancer Stage | Prior Cancer Therapy | HRG deltaCt (mRNA) | Treatment | PFS* (days) | OS* (days) | Best Response |
|---|---|---|---|---|---|---|---|
| 73 | IV | CISPLATIN + GEMCITABINE | 2.59 | Placebo + Erlotinib | 43 | 140(c) | PD |
| 74 | IV | CISPLATIN + GEMCITABINE | 5.08 | U3-1287 9 mg/kg + Erlotinib | 65 | 345(c) | PR |
| 75 | IV | CISPLATIN + PEMETREXED | 5.39 | Placebo + Erlotinib | 44 | 71 | PD |
| 76 | IV | CARBOPLATIN + PACLITAXEL | 2.98 | U3-1287 18 mg/kg + Erlotinib | 1(c) | 52(c) | NE |
| 77 | IV | CISPLATIN + DOCETAXEL; PEMETREXED | 5.41 | Placebo + Erlotinib | 248 | 379(c) | SD |
| 78 | IV | CARBOPLATIN + PACLITAXEL; DOCETAXEL | 5.78 | Placebo + Erlotinib | 42 | 57 | PD |
| 79 | IV | CARBOPLATIN + PACLITAXEL; CISPLATIN + PEMETREXED | 5.06 | Placebo + Erlotinib | 247(c) | 427(c) | PR |
| 80 | IV | CISPLATIN + OTHER: ETOPOSIDE | 4.01 | Placebo + Erlotinib | 38 | 311(c) | PD |
| 81 | IV | CISPLATIN + DOCETAXEL | 3.66 | Placebo + Erlotinib | 168 | 330(c) | PR |
| 82 | IV | CISPLATIN + DOCETAXEL | 5.85 | Placebo + Erlotinib | 27 | 27 | NE |
| 83 | IV | CISPLATIN + GEMCITABINE | 4.58 | Placebo + Erlotinib | 173(c) | 328(c) | SD |
| 84 | IV | CISPLATIN + GEMCITABINE; OTHER: TAXOTERE | 1.98 | U3-1287 9 mg/kg + Erlotinib | 85 | 185 | SD |
| 85 | IV | CISPLATIN + PEMETREXED | 3.32 | Placebo + Erlotinib | 167 | 323(c) | SD |
| 86 | IV | CISPLATIN + GEMCITABINE | 4.2 | U3-1287 18 mg/kg + Erlotinib | 168(c) | 321(c) | SD |
| 87 | IV | CISPLATIN + DOCETAXEL; CISPLATIN + DOCETAXEL | 4.63 | U3-1287 18 mg/kg + Erlotinib | 83 | 246(c) | SD |
| 88 | IV | CISPLATIN + GEMCITABINE; PEMETREXED | 3.85 | U3-1287 9 mg/kg + Erlotinib | 43 | 522(c) | PD |
| 89 | IIIB | CISPLATIN + CARBOPLATIN + PACLITAXEL + BEVACIZUMAB | 8.1 | U3-1287 9 mg/kg + Erlotinib | 81 | 174 | SD |
| 90 | IV | CARBOPLATIN + GEMCITABINE + PACLITAXEL + DOCETAXEL | 3.04 | Placebo + Erlotinib | 34 | 46 | PD |
| 91 | IIIB | CISPLATIN + CARBOPLATIN + GEMCITABINE | 5.04 | Placebo + Erlotinib | 43 | 221 | PD |
| 92 | IV | CARBOPLATIN + GEMCITABINE; DOCETAXEL | 3.7 | U3-12.87 18 mg/kg + Erlotinib | 85 | 278(c) | SD |
| 93 | IV | CARBOPLATIN + CISPLATIN + OTHER: DOXORUBICIN + OTHER: ETOPOSIDE | 1.43 | Placebo + Erlotinib | 78 | 123 | PD |
| 94 | IV | CISPLATIN + OTHER: ETOPOSIDE; OTHER: CAMPTOTHECIN | 3.43 | Placebo + Erlotinib | 70 | 322 | PD |
| 95 | IV | CISPLATIN + OTHER: ETOPOSIDE; OTHER:TAXOTER | 6.71 | U3-1287 18 mg/kg + Erlotinib | 165(c) | 336(c) | PR |
| 96 | IV | CARBOPLATIN | 2.3 | Placebo + Erlotinib | 44 | 81 | PD |
| 97 | IV | CARBOPLATIN + PACLITAXEL; CISPLATIN + OTHER: ETOPOSID, DOXORUBICIN | 3.46 | U3-1287 18 mg/kg + Erlotinib | 129 | 129 | SD |

-continued

| Patient # | Cancer Stage | Prior Cancer Therapy | HRG deltaCt (mRNA) | Treatment | PFS* (days) | OS* (days) | Best Response |
|---|---|---|---|---|---|---|---|
| 98 | IV | CARBOPLATIN + OTHER: ETOPOSIDE; CISPLATIN + DOCETAXEL + OTHER: CYCLOPHOSPHAMIDE | 2.81 | U3-1287 9 mg/kg + Erlotinib | 173 | 267(c) | SD |
| 99 | IV | CISPLATIN + PACLITAXEL; CARBOPLATIN + GEMCITABINE + PACLITAXEL | 3.97 | U3-1287 9 mg/kg + Erlotinib | 171(c) | 351(c) | PR |
| 100 | IV | CISPLATIN + OTHER: ETOPOSIDUM | 2.93 | U3-1287 18 mg/kg + Erlotinib | 7 | 7 | NE |
| 101 | IV | CISPLATIN + OTHER: ETOPOSID | 0.1 | U3-1287 9 mg/kg + Erlotinib | 141 | 141 | SD |

What is claimed is:

1. A method of treating a human subject harboring head and neck cancer comprising administering a treatment comprising an anti-HER3 antibody to a human subject diagnosed with head and neck cancer, wherein the head and neck cancer has progressed on at least one prior systemic therapy and heregulin (HRG) gene expression of the head and neck cancer at an mRNA level is assessed as high; wherein the mRNA level is assessed using quantitative reverse transcriptase polymerase chain reaction (qRT-PCR) and identified as high if a delta Ct (dCt) value of 5.0 or less is observed from a biological sample taken from the subject diagnosed with head and neck cancer, and wherein HRG is the only gene for which gene expression at the mRNA level is assessed.

2. The method of claim 1 in which the dCt value is selected from the group consisting of 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, −0.1, −0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, −2.1, −2.2, −2.3, −2.4, −2.5, −2.6, −2.7, −2.8, −2.9, −3.0, −3.1, −3.2, −3.3, −3.4, −3.5, −3.6, −3.7, −3.8, −3.9, −4.0, −4.1, −4.2, −4.3, −4.4, −4.5, −4.6, −4.7, −4.8, −4.9, −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2 and −7.3.

3. The method of claim 1, wherein the dCt value is in a range of from about 2.7 to about 4.1.

4. The method of claim 1, wherein the subject harbors wild-type EGFR.

5. The method of claim 1 in which the biological sample comprises a tumor sample.

6. The method of claim 5, in which a tumor tissue or fragment thereof for or with which the HRG gene expression is assessed has been removed from the subject prior to any therapy.

7. The method of claim 1 in which the anti-HER3 antibody is selected from the group consisting of patritumab, duligotumab (MEHD-7945A), seribantumab (MNI-121), MM-111, LJM716, RG-7116, tri-specific anti-EGFR/ERBB3 zybody, and huHER3-8.

8. The method of claim 1 in which the treatment further comprises administering an anti-HER3 antibody in combination with one or more of (i) a HER inhibitor, (ii) a chemotherapy, (iii) radiation, and (iv) an other targeted agent.

9. The method of claim 8, wherein the HER inhibitor is selected from the group consisting of trastuzumab, T-DM1, lapatinib, pertuzumab, cetuximab, panitumumab gefitinib, afatinib, dacomitinib, KD-019 and erlotinib.

10. The method of claim 8, wherein the chemotherapy is selected from the group consisting of cisplatin, carboplatin, gemcitabine, pemetrexed, irinotecan, 5-fluoruracil, paclitaxel, docetaxel, and capecitabine.

11. The method of claim 8, wherein the anti-HER3 antibody is administered in combination with (i) cetuximab and (ii) cisplatin or carboplatin.

12. The method of claim 11, wherein the anti-HER3 antibody is patritumab.

13. The method of claim 1, in which the dCt value is in a range of from about −7.3 to about 5.0.

14. The method of claim 1, wherein the HRG gene expression is assessed using an FDA-approved test.

* * * * *